US012805851B2

(12) United States Patent
Zollinger et al.

(10) Patent No.: US 12,805,851 B2
(45) Date of Patent: Nov. 24, 2026

(54) MANIFOLD AND TRAY FOR COLLECTING A TISSUE SAMPLE

(71) Applicant: Stryker Corporation, Kalamazoo, MI (US)

(72) Inventors: Michael Zollinger, Chelsea, MI (US); Michael Peterson, Richland, MI (US); Jacob C. Foor, Kalamazoo, MI (US)

(73) Assignee: Stryker Corporation, Portage, MI (US)

( * ) Notice: Subject to any disclaimer, the term of this patent is extended or adjusted under 35 U.S.C. 154(b) by 920 days.

(21) Appl. No.: 17/778,625

(22) PCT Filed: Nov. 6, 2020

(86) PCT No.: PCT/US2020/059288
§ 371 (c)(1),
(2) Date: May 20, 2022

(87) PCT Pub. No.: WO2021/101731
PCT Pub. Date: May 27, 2021

(65) Prior Publication Data

US 2022/0409191 A1 Dec. 29, 2022

Related U.S. Application Data

(60) Provisional application No. 63/008,026, filed on Apr. 10, 2020, provisional application No. 62/937,931, filed on Nov. 20, 2019.

(51) Int. Cl.
*A61B 10/02* (2006.01)
*A61M 1/00* (2006.01)

(52) U.S. Cl.
CPC ........... *A61B 10/0283* (2013.01); *A61M 1/79* (2021.05); *A61M 2205/7545* (2013.01)

(58) Field of Classification Search
CPC .. A61B 10/0283; A61B 10/0096; A61M 1/79; A61M 2205/7545; A61M 1/71
See application file for complete search history.

(56) References Cited

U.S. PATENT DOCUMENTS 4,376,053 A 3/1983 Bullock et al.
4,643,197 A 2/1987 Greene et al.
(Continued)

FOREIGN PATENT DOCUMENTS

CN 101438969 A 5/2009
CN 103096814 A 5/2013
(Continued)

OTHER PUBLICATIONS

English language abstract for WO 2004/075740 A1 extracted from espacenet.com database on Aug. 19, 2024, 2 pages.
(Continued)

*Primary Examiner* — Rene T Towa
(74) *Attorney, Agent, or Firm* — Howard & Howard Attorneys PLLC

(57) ABSTRACT

A tray and a manifold for collecting a tissue sample under influence of a vacuum. The manifold includes a sleeve, and the tray includes a sealing member configured to be removably positioned in sealing engagement with the opening. A basket defining a tissue collecting cavity, and a base portion includes at least one rib disposed within said tissue collecting cavity. The rib(s) define pockets arranged in series in the proximal-to-distal direction so as to provide low pressure regions when the tray is being removed from the sleeve. The rib(s) may be transverse to a longitudinal axis, and/or arcuate in a shape complimentary to the base portion. The base portion defines porous features that may be arranged in groupings A sealing edge in sealing engagement with an
(Continued)

upper barrier of the sleeve may delay an onset of airflow entering the tissue collecting cavity.

20 Claims, 15 Drawing Sheets

(56) References Cited

U.S. PATENT DOCUMENTS

| | | | | |
|---|---|---|---|---|
| 5,061,452 | A * | 10/1991 | Yamamoto | G01N 1/36 425/117 |
| 5,256,160 | A | 10/1993 | Clement | |
| 5,358,692 | A | 10/1994 | Reynolds | |
| 5,624,418 | A | 4/1997 | Shepard | |
| 5,797,742 | A | 8/1998 | Fraker | |
| 5,928,935 | A | 7/1999 | Reuss, Jr. et al. | |
| 7,244,236 | B2 | 7/2007 | Merkle | |
| 7,556,622 | B2 | 7/2009 | Mark et al. | |
| 7,615,037 | B2 | 11/2009 | Murray et al. | |
| 7,621,898 | B2 | 11/2009 | Lalomia et al. | |
| 7,715,037 | B2 | 5/2010 | Castellani et al. | |
| 7,775,973 | B2 | 8/2010 | Okada et al. | |
| 8,088,079 | B2 | 1/2012 | Kaye et al. | |
| 8,216,199 | B2 | 7/2012 | Murray et al. | |
| 8,251,916 | B2 | 8/2012 | Speeg et al. | |
| 8,465,439 | B2 | 6/2013 | Parks | |
| 8,518,002 | B2 | 8/2013 | Murray et al. | |
| 8,740,866 | B2 | 6/2014 | Reasoner et al. | |
| 8,864,682 | B2 | 10/2014 | Hibner | |
| 8,877,146 | B2 | 11/2014 | Williamson, IV et al. | |
| 8,915,897 | B2 | 12/2014 | Murray et al. | |
| 9,089,801 | B1 | 7/2015 | Gavlak et al. | |
| 9,579,428 | B1 | 2/2017 | Reasoner et al. | |
| 9,671,318 | B1 | 6/2017 | Bedoe et al. | |
| 9,782,524 | B2 | 10/2017 | Reasoner et al. | |
| 9,999,406 | B2 | 6/2018 | Hibner et al. | |
| 10,398,415 | B2 | 9/2019 | Nock et al. | |
| 10,413,280 | B2 | 9/2019 | Speeg et al. | |
| 10,471,188 | B1 | 11/2019 | Zollinger et al. | |
| 2003/0125639 | A1 | 7/2003 | Fisher et al. | |
| 2005/0189288 | A1 | 9/2005 | Hershberger et al. | |
| 2006/0189950 | A1 | 8/2006 | Rogers et al. | |
| 2006/0235433 | A1 | 10/2006 | Secrest et al. | |
| 2007/0191731 | A1* | 8/2007 | Kaye | A61B 10/0283 600/565 |
| 2008/0082021 | A1 | 4/2008 | Ichikawa et al. | |
| 2009/0112118 | A1 | 4/2009 | Quick, Jr. et al. | |
| 2009/0159535 | A1 | 6/2009 | Hershberger et al. | |
| 2010/0160824 | A1 | 6/2010 | Parihar et al. | |
| 2011/0106029 | A1 | 5/2011 | Garren et al. | |
| 2013/0053724 | A1 | 2/2013 | Fiebig et al. | |
| 2013/0303979 | A1 | 11/2013 | Stieglitz et al. | |
| 2014/0296894 | A1 | 10/2014 | Kojima et al. | |
| 2014/0323914 | A1 | 10/2014 | VanderWoude et al. | |
| 2015/0065913 | A1* | 3/2015 | Keller | A61B 10/0283 600/566 |
| 2017/0311935 | A1 | 11/2017 | Choung et al. | |
| 2018/0021085 | A1 | 1/2018 | Meads, Jr. et al. | |
| 2018/0235583 | A1 | 8/2018 | VanderWoude et al. | |
| 2019/0183465 | A1* | 6/2019 | Keller | G01N 1/312 |
| 2019/0195754 | A1* | 6/2019 | Keller | A61B 10/0096 |
| 2019/0343493 | A1 | 11/2019 | McCabe | |
| 2021/0162101 | A1 | 6/2021 | Zollinger et al. | |

FOREIGN PATENT DOCUMENTS

| | | | |
|---|---|---|---|
| CN | 103356245 | A | 10/2013 |
| CN | 108125694 | A | 6/2018 |
| CN | 110167453 | A | 8/2019 |
| WO | 2004075740 | A1 | 9/2004 |
| WO | 2005079947 | A2 | 9/2005 |
| WO | 2013090579 | A1 | 6/2013 |
| WO | 2017075415 | A1 | 5/2017 |
| WO | 2018170233 | A1 | 9/2018 |
| WO | 2019222655 | A2 | 11/2019 |
| WO | 2020209898 | A1 | 10/2020 |

OTHER PUBLICATIONS

International Search Report for Application No. PCT/US2019/032911 dated Dec. 3, 2019, 4 pages.

International Search Report for Application No. PCT/US2020/059288 dated Apr. 13, 2021, 3 pages.

Partial International Search Report for Application No. PCT/US2020/059288 dated Feb. 18, 2021, 2 pages.

English language abstract for CN 103356245 A extracted from espacenet.com database on Jul. 16, 2024, 2 pages.

English language abstract for CN 103096814 A extracted from espacenet.com database on Jul. 14, 2025, 2 pages.

English language abstract for CN 110167453 A extracted from espacenet.com database on Jul. 14, 2025, 2 pages.

English language abstract for CN 108125694 A extracted from espacenet.com database on Dec. 29, 2025, 2 1 pages.

* cited by examiner

MANIFOLD AND TRAY FOR COLLECTING A TISSUE SAMPLE

PRIORITY CLAIM AND RELATED APPLICATIONS

This application is a U.S. National Stage Patent Application of International Patent Application No. PCT/US2020/059288, filed Nov. 6, 2020, which claims priority to and all the benefits of U.S. Provisional Application No. 62/937,931, filed Nov. 20, 2019, and U.S. Provisional Application No. 63/008,026, filed Apr. 10, 2020, the entire contents of each is hereby incorporated by reference. This application is related to International Application No. PCT/US2019/032911, filed May 17, 2019, the entire contents of which is hereby incorporated by reference.

TECHNICAL FIELD

The present disclosure is generally directed to devices, systems, and methods for surgical procedures, and more specifically, but not exclusively, surgical procedures involving collecting a tissue sample under suction with a medical waste collection assembly.

BACKGROUND

Certain surgical procedures include the removal of a tissue sample for evaluation. For example, a polypectomy procedure involves removal of a polyp from surgical site within the patient, such as the colon or the endometrial tissue that lines the uterus. Often the polyp is aspirated with suction applied at surgical site with a medical waste collection assembly. Retrieving the polyp once collected in the suction path is an area of particular interest and development. Many known systems and methods are associated with several shortcomings, including increased time and inconvenience during the surgical procedure, potential exposure to hazardous medical waste, inability to collect multiple tissue samples, among others. Therefore, there is a need in the art for an improved manifold and methods for collecting the tissue sample with the manifold and the medical waste collection assembly.

BRIEF DESCRIPTION OF THE DRAWINGS

Advantages of the present disclosure will be readily appreciated as the same becomes better understood by reference to the following detailed description when considered in connection with the accompanying drawings.

SUMMARY

Figure 1:
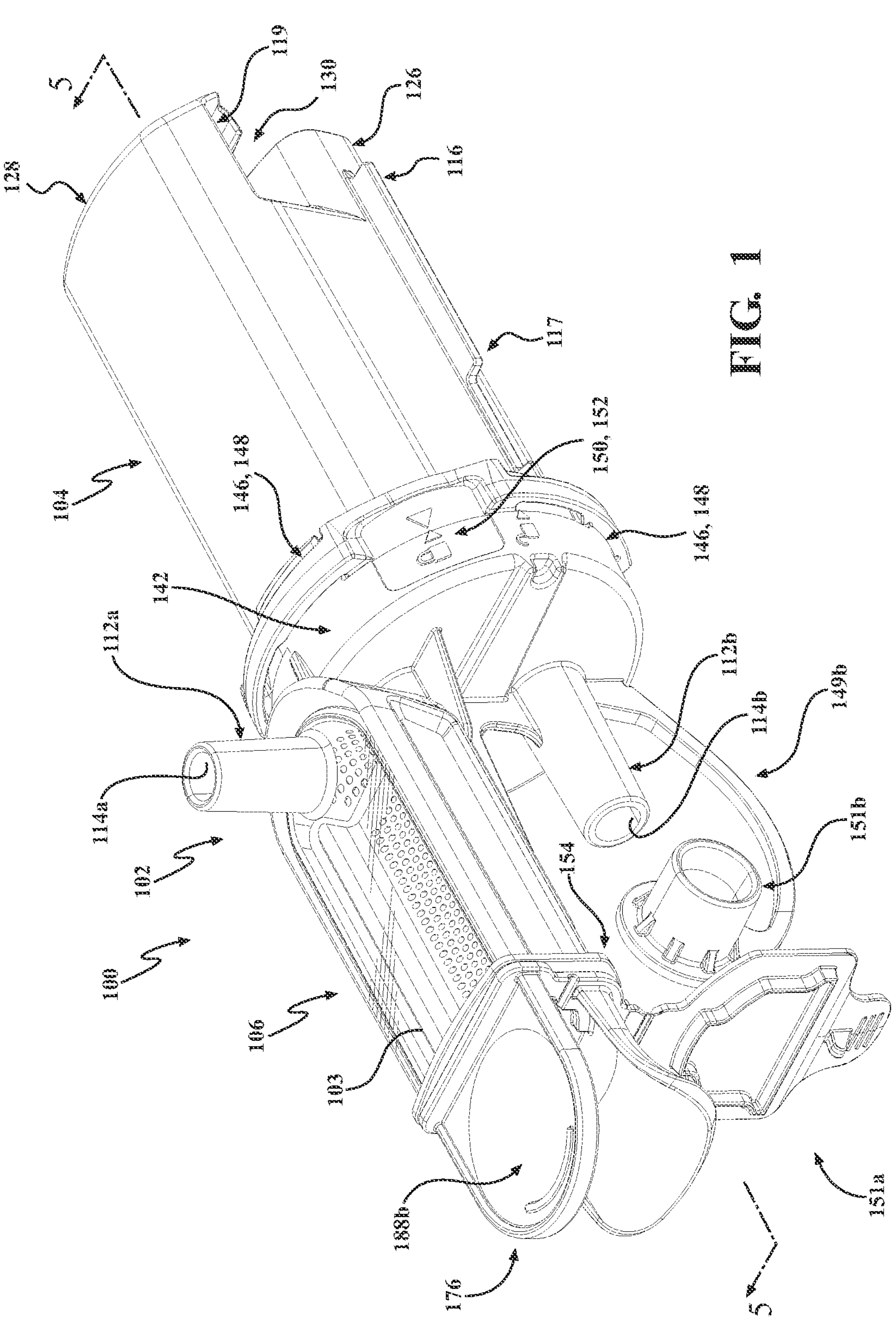
FIG. 1 a perspective view of a manifold.

A first aspect of the present disclosure is directed to a tray configured to collect a tissue sample under influence of a vacuum by being removably positioned within a sleeve having an opening. The tray includes a sealing member configured to be positioned in sealing engagement with the opening when the tray is removably positioned within the sleeve. A basket extends from the sealing member and includes a base portion and opposing side portions coupled to the base portion to collectively define a tissue collecting cavity. The base portion defines porous features for collecting the tissue sample with the tissue collecting cavity. The base portion includes ribs disposed within the tissue collecting cavity.

A second aspect of the present disclosure is directed to a tray configured to collect a tissue sample under influence of a vacuum by being removably positioned within a sleeve having an opening. The tray includes a sealing member configured to be positioned in sealing engagement with the opening when the tray is removably positioned within the sleeve. A basket extends from the sealing member and includes a base portion and opposing side portions coupled to the base portion to collectively define a tissue collecting cavity. The base portion defines porous features for collecting the tissue sample with the tissue collecting cavity. The base portion includes a rib extending between the opposing side portions and dividing the tissue collecting cavity into pockets.

A third aspect of the present disclosure is directed to a tray configured to collect a tissue sample under influence of a vacuum by being removably positioned within a sleeve having an opening. The tray includes a sealing member configured to be positioned in sealing engagement with the opening when the tray is removably positioned within the sleeve. A basket extends from the sealing member and has a length greater than a width such that the basket is elongate. The basket includes a base portion and opposing side portions coupled to the base portion to collectively define a tissue collecting cavity. The base portion defining porous features for collecting the tissue sample with the tissue collecting cavity. The base portion includes a rib within the tissue collecting cavity. The rib is elongate and oriented on an axis transverse to a longitudinal axis.

A fourth aspect of the present disclosure is directed to a tray configured to collect a tissue sample under influence of a vacuum by being removably positioned within a sleeve having an opening. The tray includes a sealing member configured to be positioned in sealing engagement with the opening when the tray is removably positioned within the sleeve. A basket extends from the sealing member and includes a base portion and opposing side portions coupled to the base portion to collectively define a tissue collecting cavity. The base portion is defined between an upper surface opposite a lower surface, and includes a rib extending upwardly from the upper surface by a distance sufficient to create a pocket that is a low pressure region as the tray is removed from within the sleeve.

A fifth aspect of the present disclosure is directed to a tray configured to collect a tissue sample under influence of a vacuum by being removably positioned within a sleeve having an opening. The tray includes a sealing member configured to be positioned in sealing engagement with the opening when the tray is removably positioned within the sleeve. A basket extends includes a proximal portion extending from the sealing member, opposing side portions coupled to the proximal portion, a base portion coupled to the opposing side portions, and a distal portion coupled to the base portion and the opposing side portions. The proximal portion, opposing side portions, the base portion, and the distal portion collectively define a tissue collecting cavity with the base portion defining porous features for collecting the tissue sample with the tissue collecting cavity. A rib that defines at least two pockets disposed within the tissue collecting cavity and arranged in series between the proximal portion and the distal portion. The pockets are associated with low pressure regions as the tray is removed from within the sleeve.

A sixth of the present disclosure is directed to a tray configured to collect a tissue sample under influence of a vacuum by being removably positioned within a sleeve having an opening. The tray includes a sealing member configured to be positioned in sealing engagement with the opening when the tray is removably positioned within the sleeve. A basket extends from the sealing member and includes a base portion and opposing side portions coupled to the base portion to collectively define a tissue collecting cavity. The base portion includes a rib dividing the tissue collecting cavity into pockets. The base portion defines porous features in each pocket. Each pocket includes groupings of the porous features in which the porous features are equally spaced apart from one another by a first distance. The groupings are spaced apart from one another by a second distance greater than the first distance.

A seventh aspect of the present disclosure is directed to a tray configured to collect a tissue sample under influence of a vacuum by being removably positioned within a sleeve having an opening. The tray includes a sealing member configured to be positioned in sealing engagement with the opening when the tray is removably positioned within the sleeve. A shelf portion extends from the sealing member and is sized and shaped complementary to the sleeve so as to be disposed within the sleeve when the sealing member is in sealing engagement with the opening. A basket includes a proximal portion extending from the shelf portion, opposing side portions coupled to the proximal portion, a base portion coupled to the opposing side portions, and a distal portion coupled to the base portion and the opposing side portions. The proximal portion, opposing side portions, the base portion, and the distal portion collectively define a tissue collecting cavity with the base portion defining porous features for collecting the tissue sample with the tissue collecting cavity. A sealing edge of the proximal portion is coplanar with an upper surface of the shelf portion.

An eighth aspect of the present disclosure is directed to a tray configured to collect a tissue sample under influence of a vacuum by being removably positioned within a sleeve having an opening. The tray includes a sealing member configured to be positioned in sealing engagement with the opening when the tray is removably positioned within the sleeve. A shelf portion extends from the sealing member and being sized and shaped complementary to the sleeve so as to be disposed within the sleeve when the sealing member is in sealing engagement with the opening. A basket includes a proximal portion extending from the shelf portion, opposing side portions coupled to the proximal portion, a base portion coupled to the opposing side portions, and a distal portion coupled to the base portion and the opposing side portions. The proximal portion, opposing side portions, the base portion, and the distal portion collectively define a tissue collecting cavity with the base portion defining porous features for collecting the tissue sample with the tissue collecting cavity. The proximal portion extends from the shelf portion by at least five millimeters such that, as the tray is beginning to be removed from the sleeve, ingress of air into the sleeve is prevented adjacent the proximal portion while ingress of air into the sleeve is permitted adjacent the base portion.

A ninth aspect of the present disclosure is directed to a tray configured to be removably positioned within a sleeve having an opening. The tray is configured to collect a tissue sample drawn through a first suction path. The tray includes a sealing member configured to be positioned in sealing engagement with the opening when the tray is removably positioned within the sleeve. The sealing member includes a resiliently flexible portion. A first control member extends from the sealing member, and a second control member extending from the sealing member and spaced apart from the first control member. A basket extends from the sealing member in a direction opposite the first and second control members. The basket defines porous features for collecting the tissue sample from a liquid drawn through the first suction path. The first and second control members are positioned opposite the resiliently flexible portion and configured to receive an input to resiliently and pivotably move at least a portion of the sealing member away from the opening to provide a second suction path through the opening and the sleeve.

A tenth aspect of the present disclosure is directed to a tray configured to be removably positioned within a sleeve having an opening. The tray is configured to collect a tissue sample drawn through a first suction path. The tray includes a sealing member configured to be positioned in sealing engagement with the opening when the tray is removably positioned within the sleeve. The sealing member includes an upper region and a lower region. A first control member extends from the upper region, and a second control member extends from the lower region and spaced apart from the first control member. A basket extends from the upper region in a direction opposite the first control member. The basket defines porous features for collecting the tissue sample, and no portion of the basket extends from the lower region of the sealing member. The first and second control members are configured to receive an input to pivot the lower region relative to the upper region to move the lower region of the sealing member away from the opening to provide a second suction path through the opening and the sleeve without disturbing the collected tissue sample.

An eleventh aspect of the present disclosure is directed to a tray configured to be removably positioned within a sleeve having an opening. The tray is configured to collect a tissue sample drawn through a first suction path. The tray includes a sealing member configured to be positioned in sealing engagement with the opening when the tray is removably positioned within the sleeve. The sealing member includes an upper region and a lower region separated by a living hinge including a reduced thickness portion of the sealing member. A control member extends from the upper region. A basket extending from the sealing member in a direction opposite the control member. The basket includes porous features for collecting the tissue sample. The control member is configured to receive an input to pivot the lower region relative to the upper region about the living hinge to move the lower region of the sealing member away from the opening to provide a second suction path through the opening and the sleeve.

A twelfth aspect of the present disclosure is directed to a tray configured to be removably positioned within a sleeve having an opening. The tray is configured to collect a tissue sample drawn under the influence of suction. The tray includes a sealing member configured to be positioned in sealing engagement with the opening when the tray is removably positioned within the sleeve. A control member extends from the sealing member. A basket is coupled to the sealing member and includes a base portion, opposing side portions coupled to the base portion to collectively define a tissue collecting cavity, and porous features defined within the base portion for collecting the tissue sample. The basket has a first sectional profile defined by the base portion, the opposing side portions, and a boundary between an upper aspect of the opposing side portions. The basket further includes a necked region extending from the sealing member in a direction opposite the control member. The necked region having a second sectional profile defined between a lower transition surface of the necked region and the upper aspect of the opposing side portions. The second sectional profile is smaller than the first sectional profile such that a void space is defined between the tissue collecting cavity and the sealing member.

A thirteenth aspect of the present disclosure is directed to a tray configured to be removably positioned within a sleeve having an opening. The tray is configured to collect a tissue sample drawn through a first suction path. The tray includes a sealing member configured to be positioned in sealing engagement with the opening when the tray is removably positioned within the sleeve. The sealing member includes a resiliently flexible portion. A control member extends from the sealing member and configured to receive an input to resiliently and pivotably move at least a portion of the sealing member away from the opening to provide a second suction path through the opening and the sleeve. A basket is coupled to the sealing member and includes a base portion, opposing side portions coupled to the base portion to collectively define a tissue collecting cavity, porous features within the base portion for collecting the tissue sample, and a foot including opposing rails extending along the base portion in a direction away from the tissue collecting cavity. The foot is configured to channel the second suction path.

In certain implementations, the tray may include at least two pockets, for example, four pockets. One of the pockets may be defined between the rib and said proximal portion, and/or between the rib and said distal portion. The basket may have a length greater than a width such that said basket is elongate and has a longitudinal axis, and the rib may be elongate and oriented on an axis transverse to said longitudinal axis. The rib(s) may be crescent-shaped. The porous features may be positioned between said ribs. There may be three ribs, and the ribs may be equally spaced apart from one another. More particularly, the three ribs may define four pockets of said base portion, and the porous features are within each of said four pockets. The three ribs may be parallel to one another. The base portion may be arcuate in shape and concave between said opposing side portions. The rib may be arcuate and contoured complementary to said arcuate shape of said base portion. The porous features may be arranged in at least two groupings. Each of the groupings may include at least two rows of said pores oriented longitudinally along said base portion. The ribs may separate the groupings. The above implementations may be included on any one or more of the first through thirteenth aspects of the tray.

A fourteenth aspect of the present disclosure is directed to a manifold for collecting a tissue sample through a suction tube. The manifold includes a housing having a sleeve defining an opening. The sleeve includes an inlet fitting defining an inlet bore opening into the sleeve. The manifold includes a tray. The tray may be any one or more of the first through thirteenth aspects of the tray.

A fourteenth aspect of the present disclosure is directed to a method of collecting a sample under influence of a vacuum from a medical waste collection assembly including a receiver. A suction tube is coupled to an inlet fitting of a manifold that defines an inlet bore. The manifold is positioned within an opening of the receiver. A tray is removably disposed within a sleeve in a first position such that (i) a sealing member of the tray is positioned in sealing engagement with an opening, (ii) a distal portion of the tray is positioned distal to the inlet bore, and (iii) a tissue collecting cavity of the tray opens towards the inlet bore. The medical waste collection assembly is operated with the tray in the first position, wherein the sample is drawn through a first suction path into the tissue collecting cavity. An input is provided to first and second control members to resiliently move the first and second control members towards one another. A lower portion of the sealing member moves away from the opening to provide a second suction path. The input to the first and second control members is maintained while moving the tray from the first position to a second position in which the sealing member moves away from the opening and a sealing edge of the tray remains in sealing engagement with an upper barrier defining the sleeve. The distal portion of the tray remains positioned distal to the inlet bore in the second position. The input to the first and second control members is maintained while moving the tray from the second position to a third position in which the sealing member moves further away from the opening and the sealing edge of the tray disengages the upper barrier defining the sleeve to provide a third suction path. The distal portion of the tray moves proximal to the inlet bore in the third position to eliminate the first suction path and provide a fourth suction path.

DETAILED DESCRIPTION

The aspiration of a tissue sample from within the patient may be facilitated with a medical waste collection assembly, for example, the Neptune 2® and Neptune 3® Waste Management Systems manufactured by Stryker Corporation (Kalamazoo, Mich.), and disclosed in commonly-owned U.S. Pat. Nos. 7,621,898, 8,216,199, 8,740,866, 8,915,897, 9,579,428, and 9,782,524, the entire contents of each are hereby incorporated by reference. The medical waste collection assembly, in a broadest sense, includes a vacuum pump adapted to be placed in fluid communication with a proximal end of a suction tube. A distal end of the suction tube is coupled to an instrument positioned near the surgical site. As used herein, proximal refers to a direction towards a rear of the manifold 100 and the medical waste collection assembly when engaged with the manifold 100, and distal refers to a direction towards a front of the manifold 100 and the surgical site (see FIG. 1). The desired tissue sample is resected, for example, with a snare technique, and the resected tissue sample is aspirated into suction tube towards the medical waste collection assembly.

The aspiration of semisolid and solid matter, including the tissue sample, must be captured or suitably filtered to avoid potential clogging of components of the medical waste collection assembly. The medical waste collection assembly includes a manifold receiver adapted to be removably engaged with a manifold 100. The medical waste collection assembly further includes a suction inlet adapted to be in fluid communication with an outlet opening of the manifold 100 when the manifold 100 is engaged with the manifold receiver. In one implementation, the manifold receiver may include a valve disc that is rotatable to align a bore with the suction inlet when the outlet opening engages and rotates a boss defining the bore, as disclosed within commonly-owned U.S. Pat. Nos. 7,615,037, 8,518,002, 8,915,897, and 9,579,428, the entire contents of each are hereby incorporated by reference. In another implementation, the manifold receiver may include an inlet mechanism that is translatable and includes a suction fitting configured to engage the outlet opening, as disclosed within commonly-owned U.S. Pat. No. 10,471,188, issued Nov. 12, 2019, the entire contents of which are hereby incorporated by reference. The manifold 100 is adapted to receive the suction tube to establish a suction path is established from the suction tube to the medical waste collection assembly through the manifold 100. The manifold 100, among other functions to be described, captures the semisolid and solid matter entrained within the stream being aspirated from the surgical site.

Figure 2:
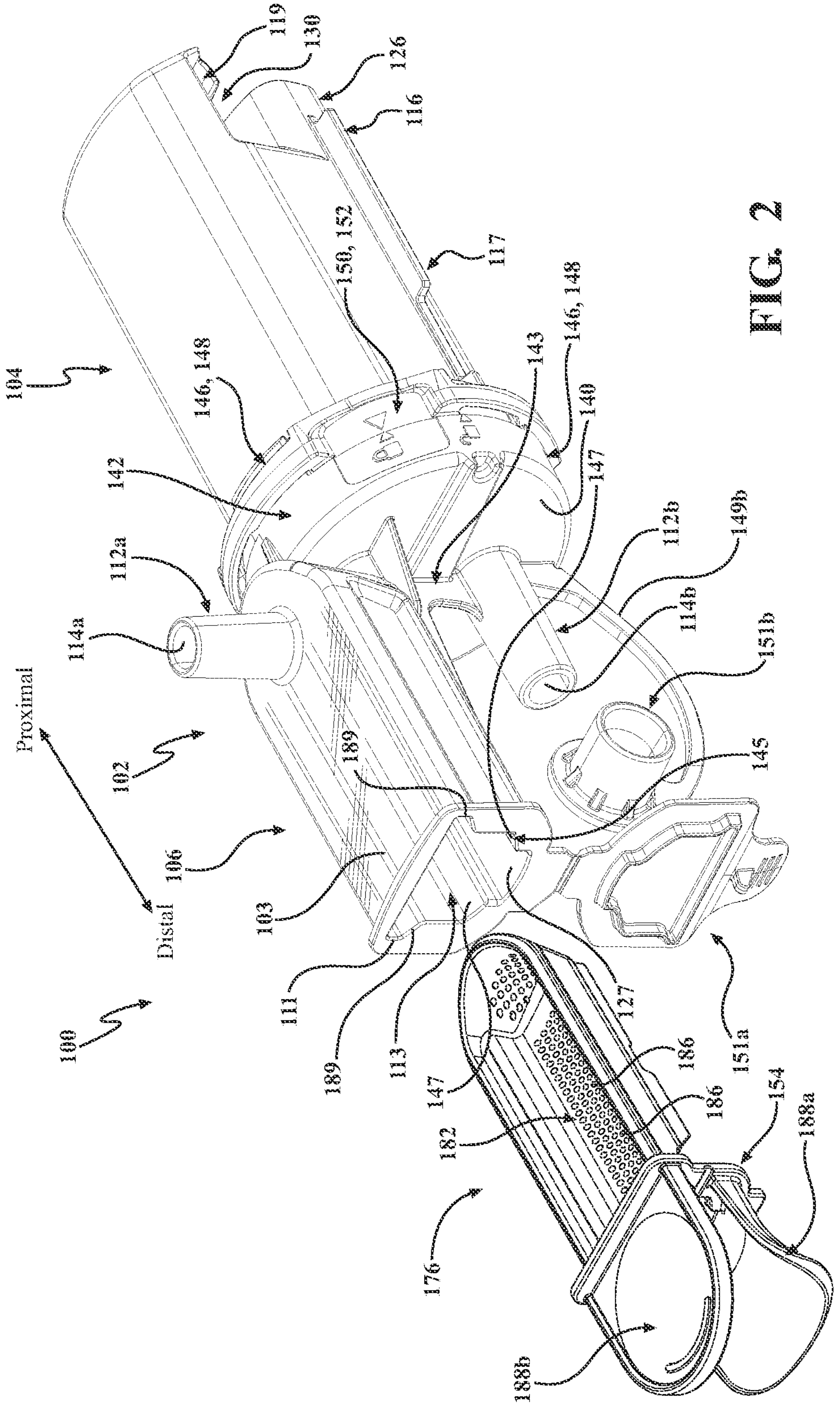
FIG. 2 is a perspective view of the manifold with a tray removed from a sleeve.

FIGS. 1 and 2 show an implementation of the manifold 100 for collecting the tissue sample. The manifold 100 includes a housing 102 adapted to be removably engaged with the manifold receiver. The housing 102 may include a trunk 104 and a cap portion 106. The manifold 100 may define a manifold volume 108 and an outlet opening 109 in fluid communication with the manifold volume 108. A seal 110 may be coupled to the housing 102 and sized to cover the outlet opening 109. The manifold volume 108 may be defined by the trunk 104 and/or the cap portion 106, and in certain implementations, the housing 102 may be an adapter for the suction tube and not define the manifold volume 108. The trunk 104 may include features configured to engage complementary features of the manifold receiver of the medical waste collection assembly. The features of the housing 102, described in greater detail in the aforementioned U.S. Pat. No. 10,471,188, may include an arm 116, a lock element 117, a spine 118, and/or a catch 119. The trunk 104 may include a first leg 126 and a second leg 128 spaced apart from the first leg 126 to define a void 130.

The housing 102 includes at least one inlet fitting 112*a*, 112*b* adapted to receive the suction tube. The inlet fitting(s) 112*a*, 112*b* defines a respective inlet bore 114*a*, 114*b* in fluid communication with the manifold volume 108. A valve 132 may be coupled to the housing 102 and configured to prevent backflow from the manifold volume 108. The valve 132 may be coupled to the cap portion 106. In particular, an inner or proximal surface of the cap portion 106 may include a coupler 107, such as a protrusion extending proximally. The valve 132 includes a coupler 137 complementary to the coupler 107 of the cap portion 106. The coupler 137 may be a slot sized to engage the protrusion with an interference arrangement. Additionally or alternatively, a suitable joining process such as adhesives, mechanical fastening, and the like, may be used to couple the valve 132 with the cap portion 106. The valve 132 may include a pair of flappers 135 with one flapper 135 configured to selectively cover a transfer bore 125 establishing communication between an accessory sleeve 113 to be described, and the manifold volume 108, and the other flapper 135 configured to selectively cover a second one of the inlet bores 114*b*. The valve 132 may be formed with elastic material(s) so as to resiliently deform in the proximal-to-distal direction under vacuum provided by the vacuum pump. Certain features of the valve 132 may be similar to those disclosed in U.S. Pat. No. 7,715,037, issued Nov. 10, 2009, the entire contents of which are hereby incorporated by reference. The sealing of the proximal end of the inlet and transfer bores 114*b*, 125 prevent backflow from the manifold volume 108 to the accessory sleeve 113 and the inlet bore 114*b*, respectively, and thus possible egress of the waste material.

The manifold 100 may include a filter element 133 disposed within the housing 102 and in the suction path. The filter element 133, in a broadest sense, includes structures configured to capture or collect the semisolid or solid waste material entrained within the liquid waste material being drawn through the manifold 100 under the influence of the vacuum provided by the medical waste collection system. The filter element 133 includes porous features or apertures, for example, holes, pores, and/or slots, among others. In other words, the suction path is provided from the inlet bore 114*a*, 114*b* to the suction inlet of the receiver through each of the manifold volume 108, the filter element 133, and the outlet opening 109. The filter element 133 may form a basket-shaped structure. The filter element 133 may be disposed within the manifold volume, or be disposed in a location separate from the manifold volume 108. Shapes and configurations of the filter element 133 suitable for certain implementations of the manifold 100 are disclosed in commonly-owned International Publication No. WO 2018/170233, filed Mar. 15, 2018, and International Publication No. PCT/US2019/060732, filed Nov. 11, 2019, the entire contents of each are hereby incorporated by reference. Still further, the filter element 133 may be considered optional, and manifold designs that do not include a filter element 133 are contemplated.

Figure 3:
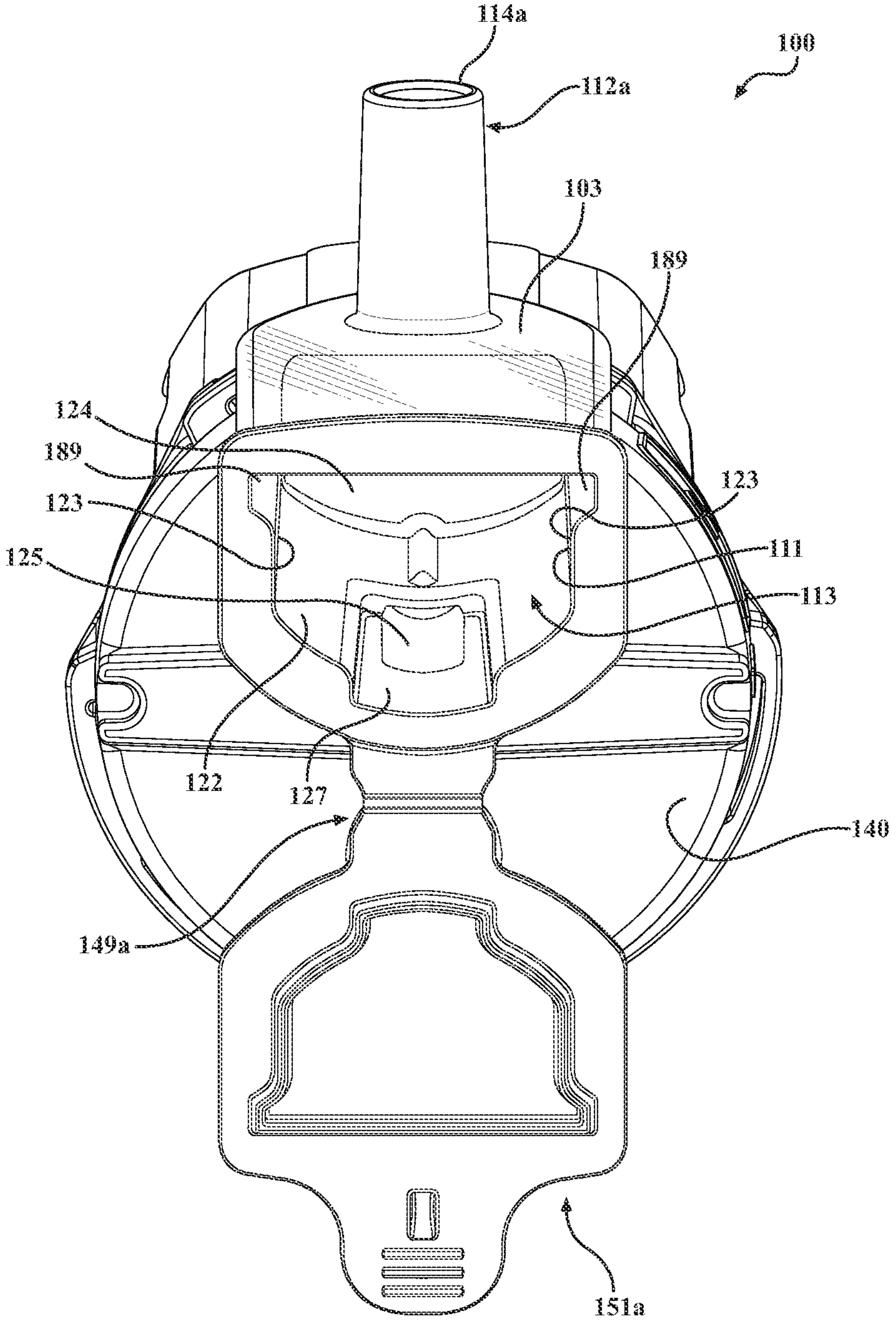
FIG. 3 is a near front elevation view of the manifold without the tray showing internal features of the sleeve.

Referring now to FIGS. 1 and 2, the cap portion 106 includes a cap head 142 and a support frame 143 positioned distal to the cap head 142. The support frame 143 may be removably coupled to or integrally formed with a cap faceplate 140 of the cap head 142. The cap portion 106 further includes an accessory sleeve 113, the first inlet fitting 112*a*, and the second inlet fitting 112*b*. More particularly, the accessory sleeve 113 may be coupled to the support frame 143, and the first inlet fitting 112*a* may extend upwardly from an upper barrier 103 with the first inlet bore 114*a* extending through the upper barrier 103. The second inlet fitting 112*b* extends distally from the cap faceplate 140 with the second inlet bore 114*b* (also referred to herein as a bypass bore) extending through the cap faceplate 140. The housing 102 of the manifold 100 further defines an accessory opening 111 opening into the accessory sleeve 113. As best shown in FIG. 3, the accessory sleeve 113 may be at least partially defined by the upper barrier 103, a lower barrier 122, and opposing side barriers 123 extending between the upper barrier 103 and the lower barrier 122. The accessory sleeve 113 may be further defined by an end barrier 124 opposite the accessory opening 111. The accessory sleeve 113 is in fluid communication with the manifold volume 108 through the transfer bore 125 and an aperture 158 extending through the cap faceplate 140. More particularly, the transfer bore 125 is defined between a first end within at least one of the lower barrier 122 and the side barrier(s) 123, and a second end opening into the manifold volume, for example, the aperture 158. The accessory sleeve 113 may include locating features 145 defining a trough 127 to be described, and orientation features 189.

The manifold 100 may include a first cover 151*a* and a second cover 151*b* configured to selectively cover the accessory opening 111 and the second inlet bore 114*b*, respectively. With reference to FIGS. 1-3, the first cover 151*a* is shaped to the contour of the accessory opening 111. The first cover 151*a* may be coupled to the housing 102 with a hinge or tether 149*a*. More particularly, the first cover 151*a* may be coupled to the accessory sleeve 113 near its distal end. The first cover 151*a* may include a grip configured to be manipulated by the user to selectively position the first cover 151*a* over the accessory opening 111. The first cover 151*a* may include an inner sealing rim configured to engage the accessory opening 111 via interference engagement. With the first cover 151*a* selectively covering the accessory opening 111, the manifold 100 may be operable with the medical waste collection assembly to provide the suction path through the first inlet bore 114*a* from the suction tube coupled to the first inlet fitting 112*a*. In such an arrangement, no tray 176 may be removably positioned within the accessory sleeve 113, and the first cover 151*a* maintains suction through the manifold 100. Decoupling the first cover 151*a* from the accessory opening 111 during operation of the medical waste collection assembly may effectively break suction without requiring terminating operation of the medical waste collection assembly. The second cover 151*b* may be coupled to the housing 102 with a tether 149*b*. The second cover 151*b* is sized to be coupled via friction or interference engagement with the second inlet fitting 112*b* to selectively cover the second inlet bore 114*b* in instances where the second inlet fitting 112 is not being utilized.

The manifold 100 includes the aforementioned tray 176 configured to be removably positioned within the accessory sleeve 113. The tray 176 includes a basket 180 defining a tissue collecting cavity 182, and porous features 186 within the tissue collecting cavity 182. With the tray 176 positioned within the accessory sleeve 113, the porous features 186 are in the suction path to collect the tissue sample. The tray 176 further includes a sealing member 154 adapted to be in sealing engagement with the accessory opening 111 when the tray 176 is within the accessory sleeve 113. The sealing member 154 may include a shelf portion 155 and a flange portion 156. The shelf portion 155 extends distally from the flange portion 156 and includes an outer periphery sized to be slightly smaller than the accessory opening 111. Likewise, the outer periphery of the flange portion 156 is shaped complementary to the accessory opening 111. In particular, with the accessory opening 111 defined collectively by the upper, lower, and opposing side barriers 103, 122, 123, the outer periphery is adapted to snugly be positioned adjacent ends of each of the upper, lower, and opposing side barriers 103, 122, 123. The shelf portion 155 facilitates positioning the tray 176 within the accessory sleeve 113 and preventing loss of suction through the accessory opening 111. The flange portion 156 defines a sealing surface 157 with the sealing surface 157 adapted to contact a perimeter of the accessory opening 111. With the tray 176 within the accessory sleeve 113 and the sealing surface 157 contacting the accessory sleeve 113, suction is maintained through the suction path during operation of the medical waste collection assembly.

Figure 6:
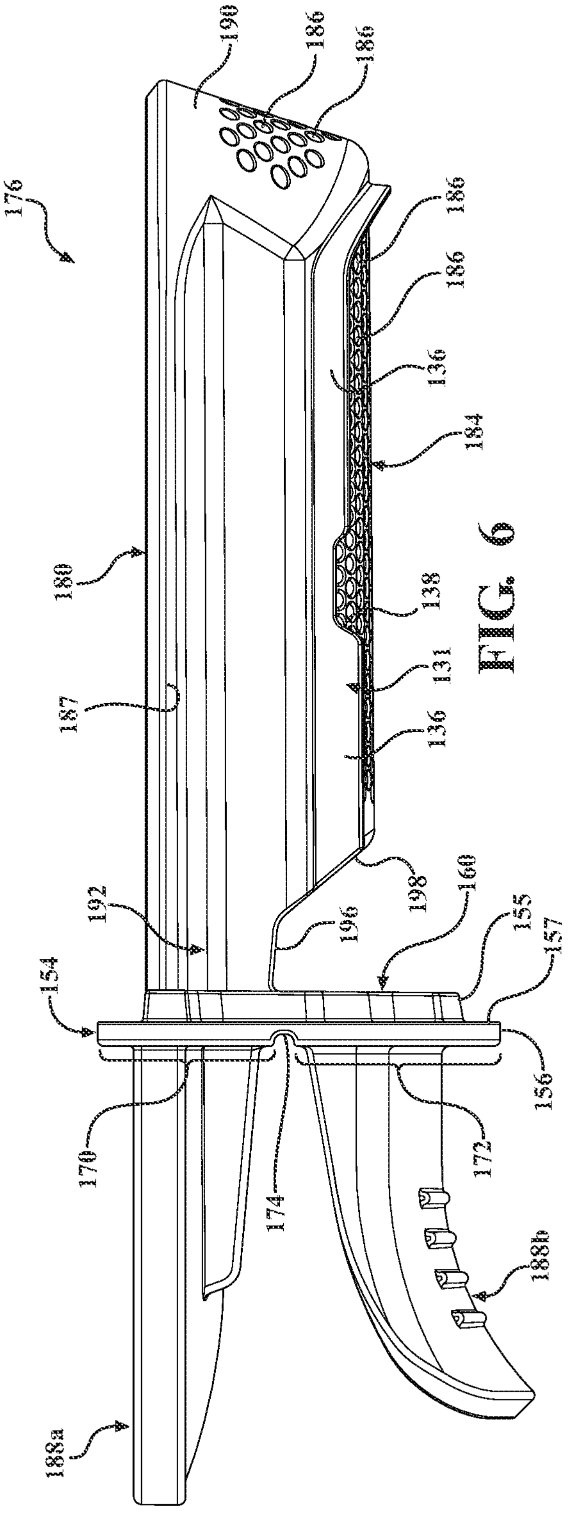
FIG. 6 is a side elevation view of the tray.

The sealing member 154 includes a resiliently flexible portion 160. The flexible portion 160 is configured to resiliently and pivotably move at least a portion of the sealing member 154 away from the accessory opening 111 to provide a second suction path in a manner to be further described. As shown in FIG. 6, the sealing member 154 may include an upper region 170 and a lower region 172, and in certain configuration, the flexible portion 160 is at least partially disposed between the upper region 170 and the lower region 172. In one example, the flexible portion 160 is a living hinge 174 being a reduced thickness portion of the sealing member 154 such that the lower region 172 may pivot relative to the upper region 170 about the living hinge 174.

Figure 4:
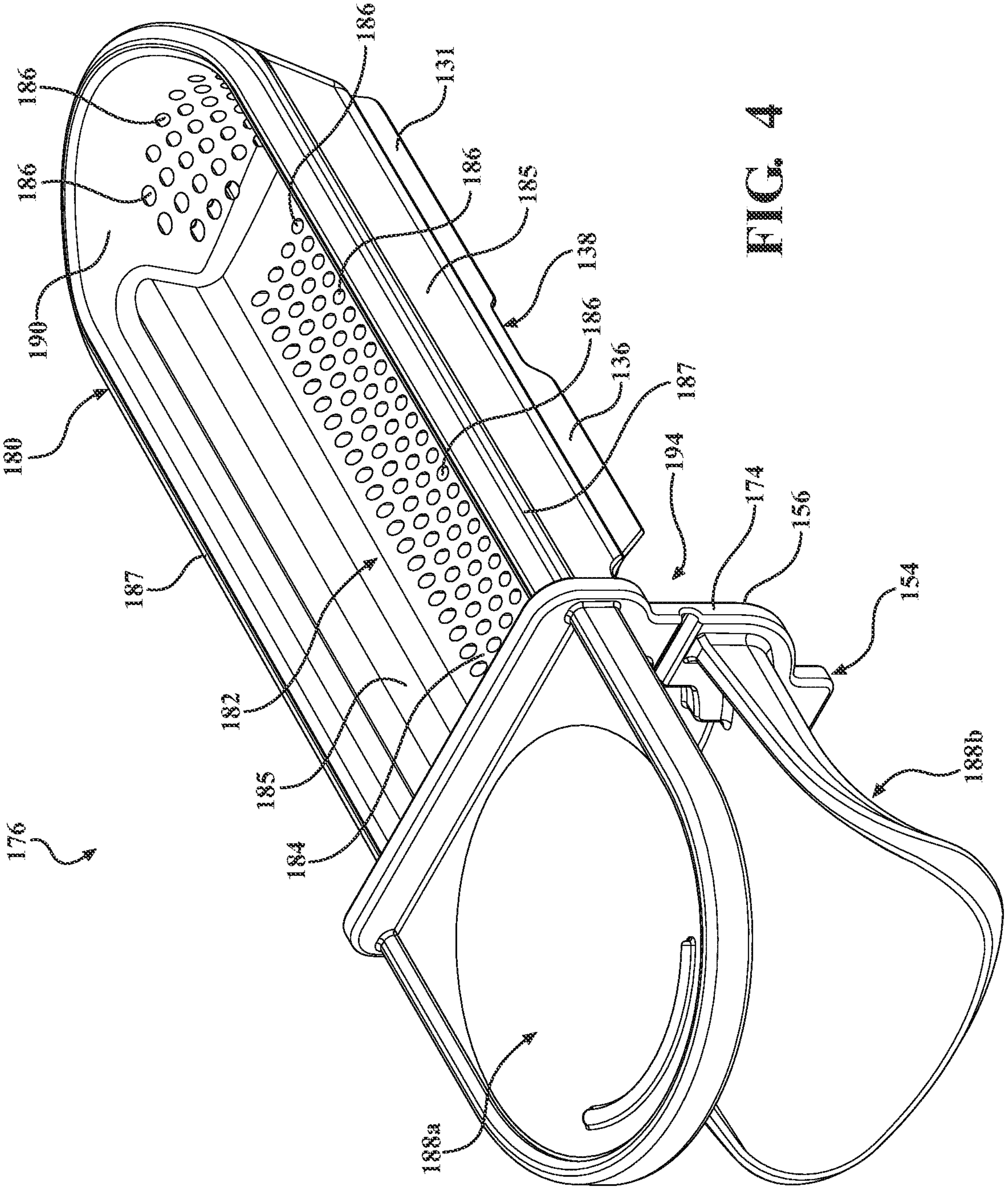
FIG. 4 is a top rear perspective view of the tray.
Figure 5:
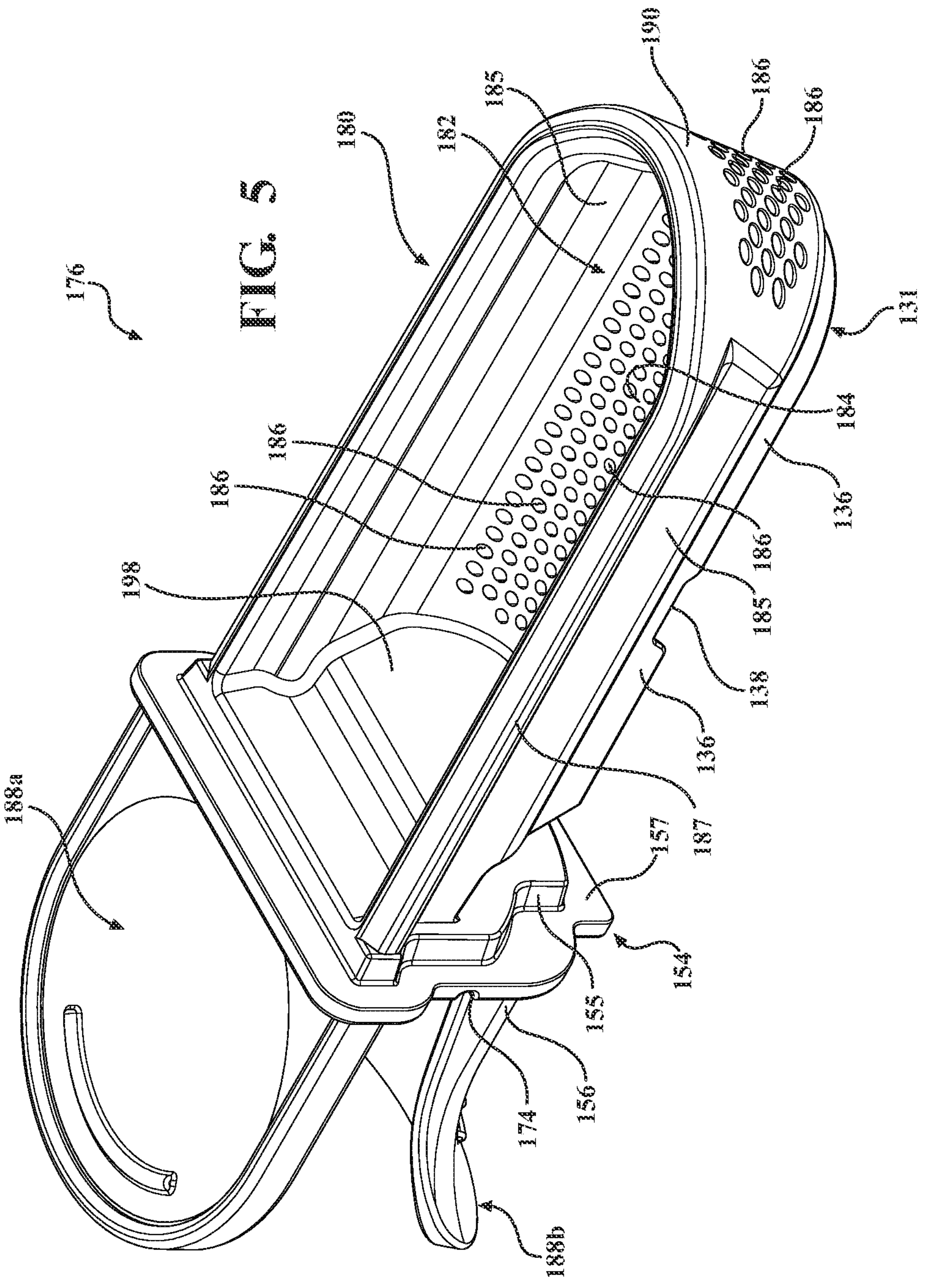
FIG. 5 is a top front perspective view of the tray.

Referring now to FIGS. 4-6, the basket 180 extends distally or in a first direction from the sealing member 154. The basket 180 includes a base portion 184, and side portion(s) 185 (also referred to herein as sides) coupled to the base portion 184. The base portion 184 may be arcuate in shape and concave between the opposing side portions 185, as shown, but alternatively may be planar or of any suitable profile. The base and side portions 184, 185 may extend from the sealing member 154 and arranged to define the tissue collecting cavity 182. For convention, the tissue collecting cavity 182 is considered to be opening away from the base portion 184 in a direction parallel to the side portions 185. The porous features 186 are defined within the base portion 184. It is contemplated that the porous features 186 may be defined within the opposing side portions 185. Further, the basket 180 may include a distal portion 190 extending between the opposing side portions 185 and further defining the tissue collecting cavity 182. The distal portion 190 may include porous features 186. The porous features 186 on the distal portion 190 are optional.

The tray 176 includes first and second control members 188*a*, 188*b* adapted to receive an input from the user. The first and second control members 188*a*, 188*b* extending from the sealing member 154 in a second direction opposite the basket 180. The second control member 188*b* may be spaced apart from the first control member 188*a* such that the first and second control members 188*a*, 188*b* are configured to be a grip pinched between fingers of the user. More specifically, the grip may be arranged to be pinched by the user to move the first control member 188*a* towards the second control member 188*b* for function to be described.

With reference to FIG. 6, the first control member 188*a* may extend from the upper region 170 of the sealing member 154, and the second control member 188*b* may extend from the lower region 170 of the sealing member 154. In such an arrangement, the first and second control members 188*a*, 188*b* may be positioned opposite the flexible portion 160 of the sealing member 154. For example, FIG. 6 shows the first and second control members 188*a*, 188*b* m positioned opposite the living hinge 174. As a result, when the first and second control members 188*a*, 188*b* are pinched between fingers of the user, the second control member 188*b* may be moved towards the first control member 188*a* with corresponding movement of the sealing surface 157 of the sealing member 154.

The arrangement of the basket 180 is further configured to facilitate movement of the second control member 188*b* towards the first control member 188*a* with the first control member 188*a* remaining generally stationary (opposed to, for example, the first control member 188*a* towards the second control member 188*b*), and thus pivot the lower region 172 of the sealing member 154 away from the accessory opening 111. In particular, the basket 180 extends from the upper region 170, and no portion of the basket 180 may extend from the lower region 172. Since the basket 180 may be snugly disposed within the accessory sleeve 113, the pinching of the first and second control members 188*a*, 188*a* in view of the positioning of the flexible portion 160 results in the pivoting of the lower region 172 of the sealing member 154 away from the accessory opening 111 (see FIG.

8). FIG. 6 shows a depth of the tissue collecting cavity 182 (approximate a height of the basket 180) being larger than a height of the upper region 170 of the sealing member 154. In order to accommodate the aforementioned arrangement, the basket 180 may include a necked region 192 having a reduced sectional profile such that such that a void space 194 is defined between the tissue collecting cavity 182 and the lower region 172 of the sealing member 154. In other words, a main portion of the basket 180 has a first sectional profile (in a plane transverse to a longitudinal axis of the tray 176), and the necked region 172 has a second sectional profile being smaller than the first sectional profile. The first sectional profile may be defined by the base portion 184 and the opposing side portions 185 (and a boundary extending between upper aspects of the opposing side portions 185). The second sectional profile may be defined by a lower transition surface 196 of the necked region 192 and the opposing side portions 185 (and the boundary extending between upper aspects of the opposing side portions 185). As a result, an interface between the basket 180 and the sealing member 154 is at the upper region 170, as best shown in FIG. 6. The lower transition surface 196 and a wall 198 may slope downwardly in the distal direction such that the depth of tissue collecting cavity 182 is generally maximized.

The tray 176 may include a foot 131 extending from the base portion 184, and more particularly extending from the base portion 184 in a direction opposite the tissue collecting cavity 182. The foot 131 may be generally U-shaped and bound the porous features 186 within the base portion 184 when viewed in bottom plan. In certain implementations, the foot 131 may be opposing rails 136 extending from the base portion 184 near the side portions 185. FIGS. 4-6 shows each of the opposing rails 136 having a slot 138. It is appreciated that the generally U-shaped foot 131, when the tray 176 is fully positioned within the accessory sleeve 113, also bounds the bore 125 in communication with the manifold volume 108 so as to channel a second suction path to be described.

With concurrent reference to FIGS. 1 and 2, the tray 176 may include orientation features 187 configured to engage the orientation features 189 of the accessory sleeve 113 to position the tray 176 within the accessory sleeve 113 in a singular relative orientation to the upper barrier 103, and in particular with the tissue collecting cavity 182 opening towards the upper barrier 103. The orientation features 189 of the accessory sleeve 113 may be considered a groove defined within each of the opposing side barriers 123. In other words, each of the side barriers 123 near the upper barrier 103 flare outwardly to define the groove. The orientation features 187 of the tray 176 may extend outwardly from the side portions 185, and in particular, near an upper aspect of the tray 176. The complementary orientation features 187, 189 may be configured to be movably engaged by sliding the rails within the grooves.

Figure 7:
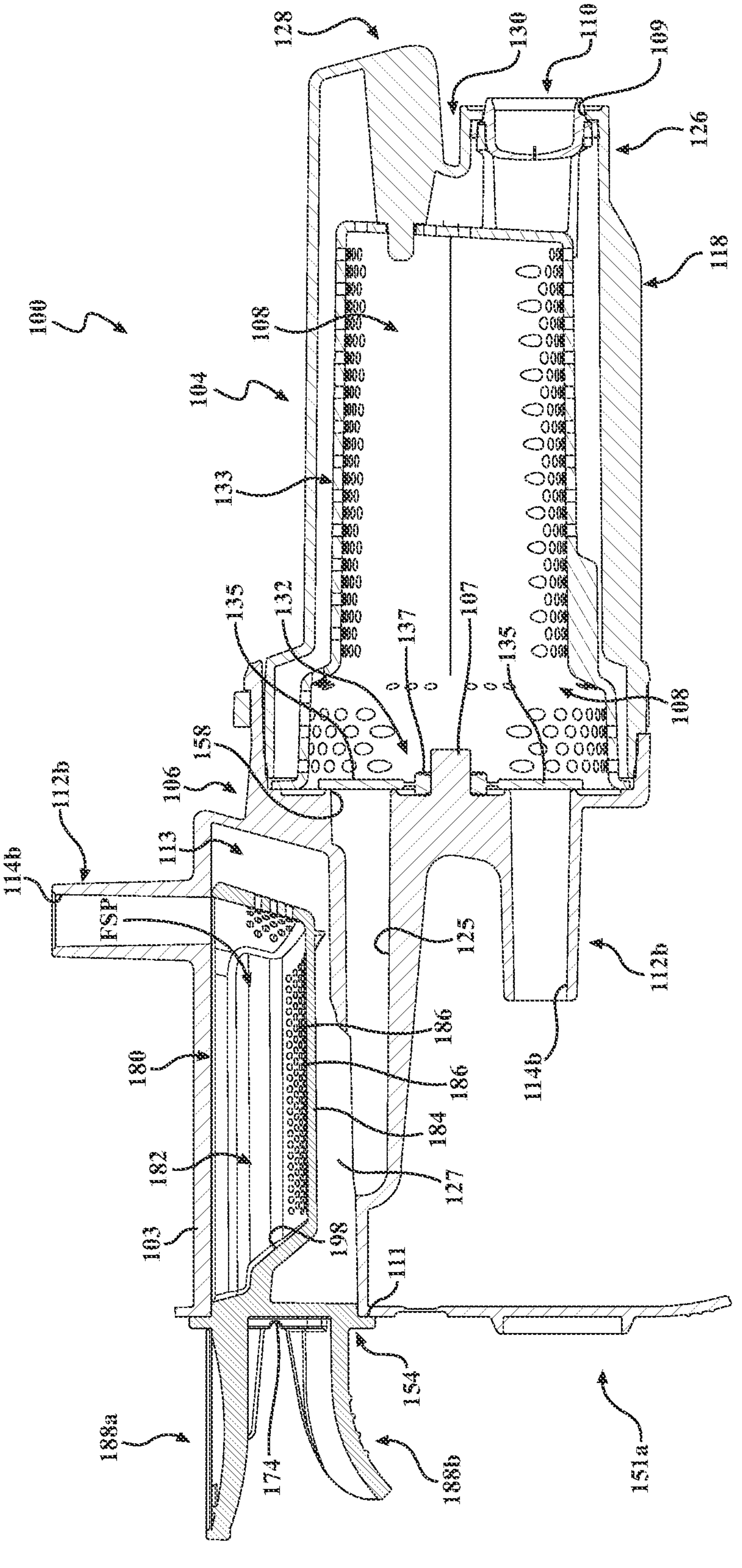
FIG. 7 is a sectional view of the manifold including the tray disposed within the sleeve with the tray in a sealing configuration.
Figure 8:
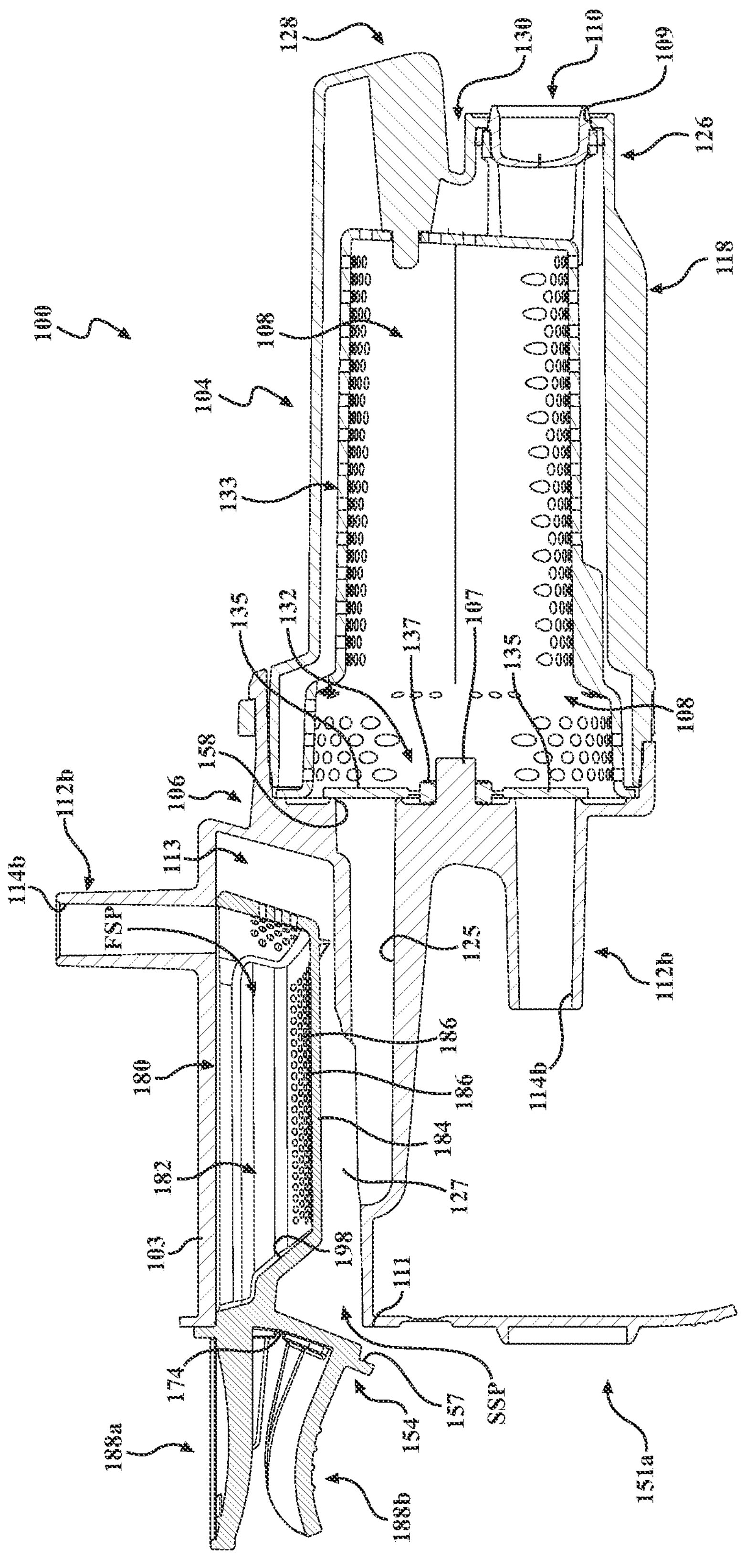
FIG. 8 is a sectional view of the manifold including the tray disposed within the sleeve with the tray in a bleed configuration.
Figure 9:
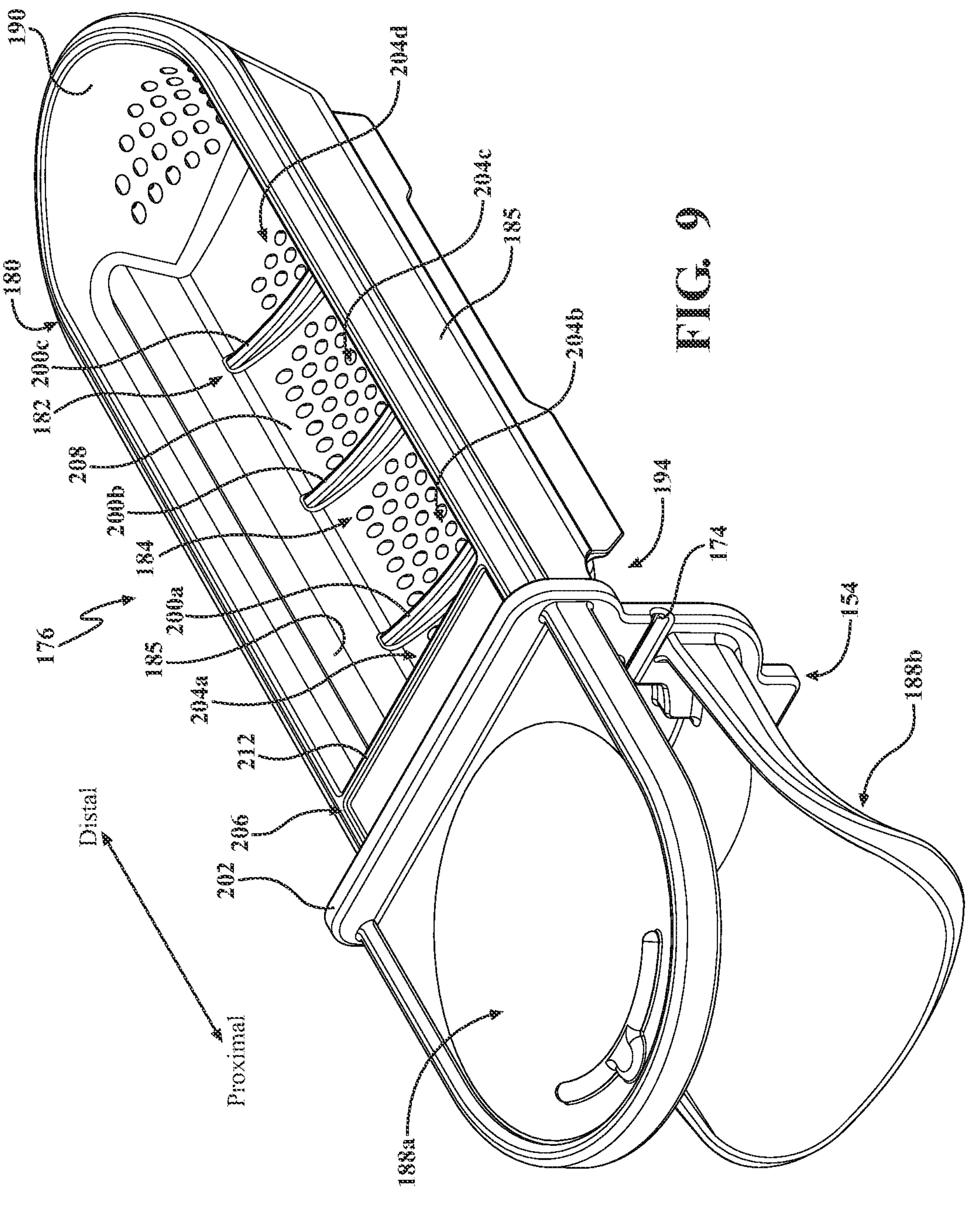
FIG. 9 is a top rear perspective view of a tray.

Referring now to FIGS. 7 and 8, with the tray 176 removably disposed within the accessory sleeve 113, (i) the sealing member 154 seals the accessory opening 111, (ii) the tissue collecting cavity 182 is positioned within the accessory sleeve 113 and opening towards the inlet bore 112*a*, and (iii) the base portion 184 and/or the side portion 185 engages the locating features 145 within the accessory sleeve 113 to provide a gap G between the base portion 184 of the tray 176 and the lower barrier 122. In such an arrangement, during operation of the medical waste collection assembly, a first suction path FSP is generated through the suction tube, the inlet bore 114*a*, the tissue collecting cavity 182, the transfer bore 125, and to the manifold volume 108 to the outlet opening 109. The tissue sample travelling through the first suction path is collected in the tray 176.

Owing to the presence of the wall 198, for example, the ramped surface, the collected tissue sample settles on the base portion 184 at a position away from the sealing member 154. Further, as mentioned, the upper barrier 103 may be transparent, as shown in FIGS. 1 and 2. As a result, a user viewing the manifold 100 from above, as is typical based on the operational height of the manifold 100 when coupled to the medical waste collection assembly, can quickly ascertain whether the tissue sample has been collected and/or the quality of the collected tissue sample. By contrast, in the absence of the wall 198 causing the collected tissue sample to settle away from the sealing member 154, the user would need to approach the manifold 100 to determine whether the tissue sample has been collected. And, of course, in the absence of the upper barrier 103 being transparent, the user would need to at least partially remove the tray 176 from the manifold 100 to determine whether the tissue sample has been collected.

The base portion 184 of the tray 176 may be arranged to rest upon or otherwise be supported by the shelf portions 147 such that the gap G is defined between an underside of the base portion 184 of the tray 176 and the upper surface of the trough 127. The gap G may be considered to be beneath the tray 176 (i.e., opposite the tissue collecting cavity 182 in the aforementioned convention). With the tray 176 positioned within the accessory sleeve 113, the gap G is in communication with the transfer bore 125 extending to the manifold volume 108. The orientation features 187 of the tray 176 may further serve as locating features to define a vertical position of the base portion 184 relative to the lower barrier 122, and hence at least partially influencing the size of the gap G. It is further noted that the upper aspect of the tray 176 is positioned adjacent to the upper barrier 103 with little distance therebetween.

Once it is desired to retrieve the collected tissue sample, the tray 176 may be slidably removed from the accessory sleeve 113 with the tissue sample disposed within the tissue collecting cavity 182. In known systems, the tissue specimen may encounter a fluid flow (and associated forces), and the tissue sample may undesirably be swept along the fluid flow and ejected from the tray. Known systems do not adequately address this issue. The manifold 100 of the present disclosure advantageously provides for generating a second suction path SSP located in a manner that the likelihood of inadvertent loss of the tissue sample is minimized. For example, the aforementioned gap G induces the second suction path to be beneath the tray 176. Further, the manifold 100 advantageously provides for the second suction path being of sufficient volume flow such that the first suction path may be temporarily limited or eliminated. In other words, the manifold 100 advantageously provides for "bleeding" or reducing suction through the first suction path, perhaps temporarily, without needing to remove the manifold 100 from the medical waste collection assembly and/or cease operation of the medical waste collection assembly.

In operation, should the user wish to reduce or eliminate the first suction path, the user provides an input to the first and second control members 188*a*, 188*b*. In particular, the user may pinch the first and second control members 188*a*, 188*b*. With particular reference to FIGS. 7 and 8, the second control member 188*b* moves or pivots (P) towards the first control member 188*a* to move the manifold 100 from a sealing configuration to a bleed configuration. More particularly, the movement of the second control member 188*b* results at least a portion of the sealing member 154 moving away from a portion of the accessory opening 111 near the lower barrier 122. For example, the lower region 172 of the sealing member 154 is pivoted relative to the upper region 170 of the sealing member 154 to move the lower region 172 away from the accessory opening 111 to provide the second suction path SSP without disturbing the collected tissue sample. The pivoting may be about the living hinge 174.

The trough 127 extending to the accessory opening 111 is exposed to atmosphere, and the second suction path SSP is provided. The gap G may be at least partially defined by the trough 127, and the second suction path SSP, owing to fluid dynamics, is directed through the gap G without encountering the tissue collecting cavity 182 of the tray 176. As shown in FIG. 7, the second suction path SSP is located from the accessory opening 111 to the bore 125 through the gap G between the base portion 184 of the tray 176 and the lower barrier 122 of the housing defining the accessory sleeve 113. Further, the foot 131 channels the second suction path SSP towards the transfer bore 125, and the slots 138 within the rails 136 impart the desired flow characteristics of the second suction path SSP. For example, the foot 131 may increase the disparity in resistance between the second suction path SSP and the first suction path FSP when the manifold 100 is in the bleed configuration such that the second suction path SSP becomes the primary suction path in the bleed configuration, and negligible suction is maintained through the suction tube. It is appreciated that maximizing of the size of the gap G (i.e., the distance from the base portion 184 to the lower barrier 122 defining the trough 127) increases the effectiveness of the bleed functionality and further reduces the likelihood of fluid flow of the second suction path SSP above the tray 176 to possibly dislodge or eject the collected tissue sample.

Owing to the lesser resistance of the fluid (e.g., the air) entering the second suction path SSP relative to the end of the suction tube disposed well upstream at the surgical site (as well as the density of the waste material in the suction tube relative to air), fluid dynamics dictate that the second suction path SSP becomes the primary suction path in the bleed configuration, and negligible suction may be maintained through the suction tube. Should the user wish to promptly reestablish the first suction path FSP as the primary (and only) suction path, the user simply releases the input provided to the first and/or second control members 188*a*, 188*b*. The resilient nature of the sealing member 154 as well as the second suction path SSP adjacent the sealing member 154 results in the sealing member 154 reengaging the accessory opening 111, and the manifold 100 reassumes the sealing configuration. Moving the manifold 100 between the sealing configuration and the bleed configuration may occur as many times as desired without undue difficulty and without needing to stop operation of the medical waste collection assembly.

Moreover, as mentioned, the second suction path SSP is located below the below the tray 176 (i.e., opposite the tissue collecting cavity 182 in the aforementioned convention). As a result, should the user wish to retrieve the tissue sample collected in the tissue collecting cavity 182, the user maintains the input to the first and second control members 188*a*, 188*b* while withdrawing the tray 176 from the accessory sleeve 113. Since the gap G is relatively larger than any distance between the upper aspect of the tray 176 positioned adjacent to the upper barrier 103, nearly an entirely of the second suction path SSP remains below the tray 176 as the tray 176 is removed. It is appreciated that the fluid flow of the second suction path SSP travelling above the tray 176 to be drawn into the tissue collection cavity 182 is lessened. As a result, the user may more confidently remove the tray 176 without risk of inadvertently losing the collected tissue sample.

The inadvertent loss of the collected tissue sample during removal of the tray 176 from the accessory sleeve 113 may be further minimized by ribs 200 disposed within the basket 180. Referring now to FIGS. 9-15, the tray 176 is shown with like numerals indicating like components to implementations previously described, and any aspect not reiterated is in the interest of brevity and should not be considered limiting.

The tray 176 includes the basket 180 defining the tissue collecting cavity 182, and the porous features 186 within the tissue collecting cavity 182. The tray 176 further includes the sealing member 154 adapted to be in sealing engagement with the accessory opening 111 when the tray 176 is within the accessory sleeve 113. The sealing member 154 includes the resiliently flexible portion 160 configured to resiliently and pivotably move at least a portion of the sealing member 154 away from the accessory opening 111 to provide the second suction path. The flexible portion 160 may be the living hinge 174 configured to facilitate pivoting of the lower region 172 relative to the upper region 170. The first and second control members 188*a*, 188*b* may be pinched between fingers of the user to move the second control member 188*b* towards the first control member 188*a* with corresponding movement of the sealing surface 157 of the sealing member 154. 154. The basket 180 may include the necked region 192 to define the void space 194 between the tissue collecting cavity 182 and the lower region 172 of the sealing member 154.

The basket 180 includes the base portion 184, and the opposing side portions 185 (also referred to herein as sides) arranged to define the tissue collecting cavity 182. The porous features 186 are defined within the base portion 184. It is contemplated that the porous features 186 may be defined within the opposing side portions 185. Further, the basket 180 may include the distal portion 190 extending between the opposing side portions 185 and further defining the tissue collecting cavity 182. The tray 176 may include the foot 131 extending from the base portion 184, for example, the opposing rails 136 extending from the base portion 184 near the side portions 185. The opposing rails 136 may have the slot 138.

With the tray 176 removably disposed within the accessory sleeve 113, the gap G between the base portion 184 of the tray 176 and the lower barrier 122 such that the first suction path FSP is generated through the suction tube, the inlet bore 114*a*, the tissue collecting cavity 182, the transfer bore 125, and to the manifold volume 108 to the outlet opening 109. The tissue sample travelling through the first suction path is collected in the tray 176. Once it is desired to retrieve the collected tissue sample, the tray 176 may be slidably removed from the accessory sleeve 113 with the tissue sample disposed within the tissue collecting cavity 182. As previously described in detail, the manifold 100 provides for generating the second suction path SSP beneath the tray 176 to move the manifold 100 from the sealing configuration to the bleed configuration, shown in FIGS. 7 and 8, respectively.

The tray 176 is configured to be moved within the accessory sleeve 113 in the proximal-to-distal direction, more particularly inserted into the accessory sleeve 113 in the distal direction and removed from the accessory sleeve 113 in the proximal direction. During removal of the tray 176 from the accessory sleeve 113, the second suction path SSP facilitates removal of the tray 176 from the accessory sleeve 113 with minimal disruption of the collected tissue sample. While most of the air is directed through second suction path SSP without encountering the tissue collecting cavity 182 of the tray 176, some air may move above or around an upper edge 202 of the sealing member 154 to within the tissue collecting cavity 182.

The base portion 184 may include at least one rib 200 disposed within the tissue collecting cavity 182. In a most general sense, the rib 200 separates a portion of the tissue collecting cavity 182 near the base portion 184 into at least two pockets 204, at least one of which is a low pressure region as the tray 176 is removed from the accessory sleeve 113. With the pocket(s) 204 being low pressure regions, any air encountering the tissue collecting cavity 182 is less likely to be associated with force sufficient to dislodge or eject the collected tissue sample. It is further understood that the rib 200 may also provide a barrier to prevent movement of the collected tissue sample along the base portion 184 prior to, during, and after removal of the tray 176 from the accessory sleeve 113.

The base portion 184 may include at least two ribs 200 disposed with the tissue collecting cavity 182. The rib(s) 200 may extend between the opposing side portions 185. With continued reference to FIGS. 9-11, the rib(s) 200 include an end coupled or integrally formed with each of the opposing side portions 185. In one example, the rib(s) are elongate and oriented on an axis transverse to the longitudinal axis LA of the tray 176 (see FIG. 11). In other words, the longitudinal axis of the tray 176 is oriented in the proximal-to-distal direction, and the rib(s) 200 are oriented transverse to the longitudinal axis LA. The arrangement provides for the rib(s) 200 generally being oriented perpendicular to the direction of removal of the tray 176 (and thus the direction of incoming air flow through the accessory sleeve 113 during removal), thereby providing the low pressure regions within the pockets 204.

Figure 11:
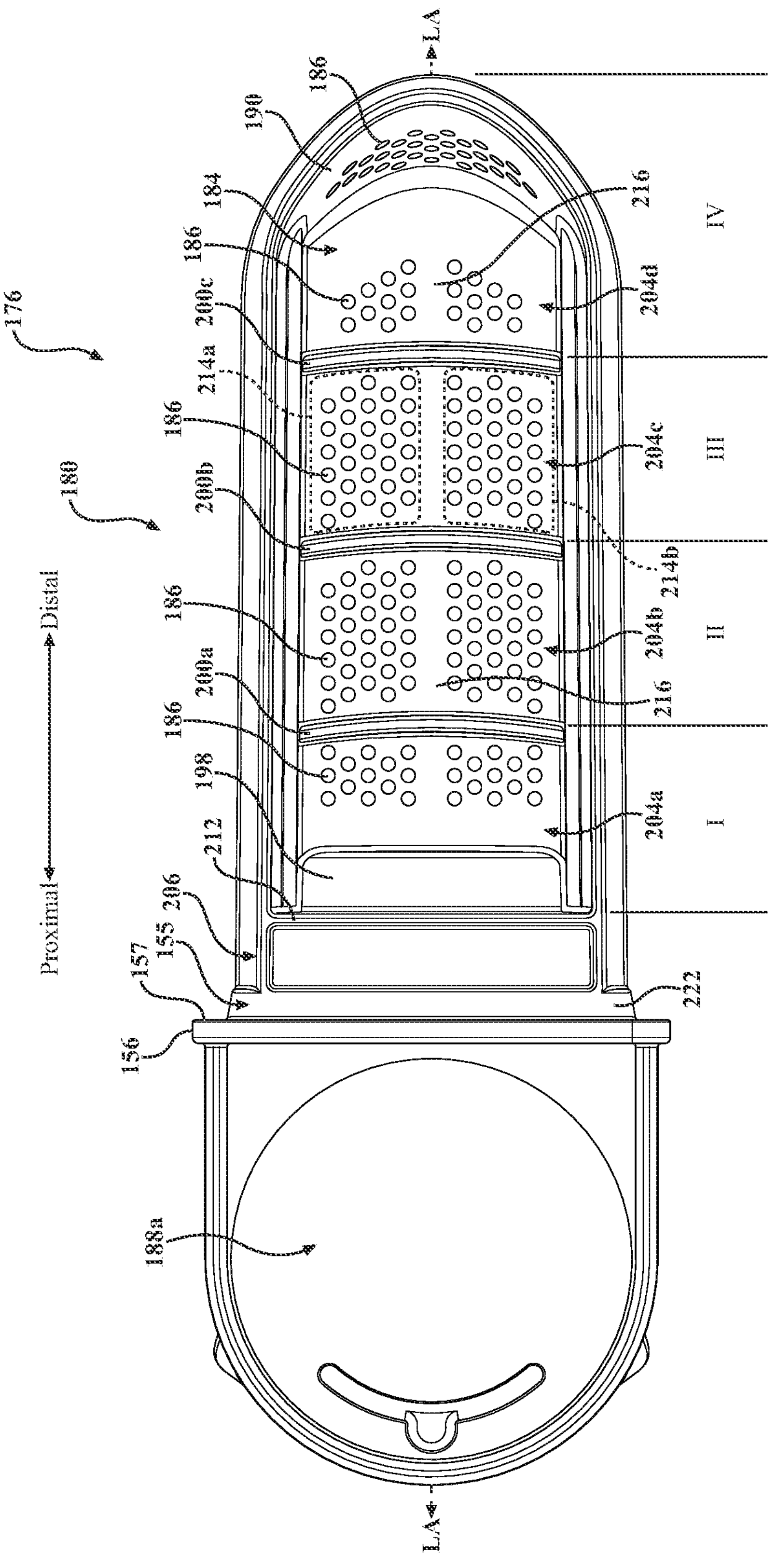
FIG. 11 is a top plan view of the tray of FIG. 9.

In certain implementations, plural ribs 200 are provided. For example, the illustrated implementation shows the base portion 184 including three ribs 200*a*-200*c* defining four pockets 204*a*-204*d*. The subsequent disclosure is directed to three ribs 200*a*-200*c*, however, any number of ribs are contemplated. The ribs 200*a*-200*c* may be equally spaced from and/or oriented parallel to one another. The ribs 200*a*-200*c* may be generally linear and continuous in arrangement, or irregularly shaped (e.g., zigzag), discontinuous, or the like. The position and orientation of the ribs 200*a*-200*c* arrange the pockets 204*a*-204*d* in series between a proximal portion 206 to be described and the distal portion 190. In other words, the pockets 204*a*-204*d* are positioned in a generally side-by-side arrangement in the proximal-to-distal direction. FIG. 11 shows the first pocket 204*a* defined between the proximal portion 206 and the first rib 200*a*, the second pocket 204*b* defined between the first rib 200*a* and the second rib 200*b*, the third pocket 204*c* defined between the second rib 200*b* and the third rib 200*c*, and the fourth pocket 204*d* defined between the third rib 200*c* and the distal portion 190. The pockets 204*a*-204*d* may be associated with regions I-IV of the tissue collecting cavity 182. The side-by-side arrangement in the proximal-to-distal direction may provide redundancy should the collected tissue sample move between pockets 204*a*-204*d* during removal of the tray 176 from the accessory sleeve 113. For example, should the collected tissue sample positioned in the first pocket 204*a* move to the second pocket 204*b*, it remains within a low pressure region (region II) of the tissue collecting cavity 182. Further air within the tissue collecting cavity 182 remains less likely to further move the collected tissue sample from the second pocket 204*b* to the third pocket 204*c*, and so on, and highly unlikely to be associated with forces sufficient to dislodge or eject the collected tissue sample.

Referring again to FIGS. 9-11, the base portion 184 may be arcuate between the opposing side portions 185. The ribs 200*a*-200*c* may also be arcuate and contoured complementary to the arcuate shape of the base portion 184. The base portion 184 may include a lower arcuate surface (not identified) opposite an upper arcuate surface 208 that partially defines the tissue collecting cavity 182. The ribs 200*a*-200*c* extend upwardly from the upper arcuate surface 208 and are contoured to the upper arcuate surface 208. In such an implementation, the ribs 200*a*-200*c* may appear crescent-shaped when in axial elevation and as generally appreciated from FIGS. 9 and 10. The ribs 200*a*-200*c* may extend upwardly from the upper arcuate surface 208 by one-half, one, two, or three, or more millimeters (as measured vertically at the longitudinal axis). In one implementation, the ribs 200*a*-200*c* extend upwardly by approximately one millimeter. In another convention, the ribs 200*a*-200*c* may extend upwardly from the upper arcuate surface 208 by less than ten percent of the depth of the tissue collecting cavity 182. Additionally or alternatively, the ribs 200*a*-200*c* may extend upwardly from the upper arcuate surface 208 such that at least substantially an entirety of the ribs 200*a*-200*c* are below an interface 210 wherein the opposing side portions 185 transition to the base portion 184.

Figure 15:
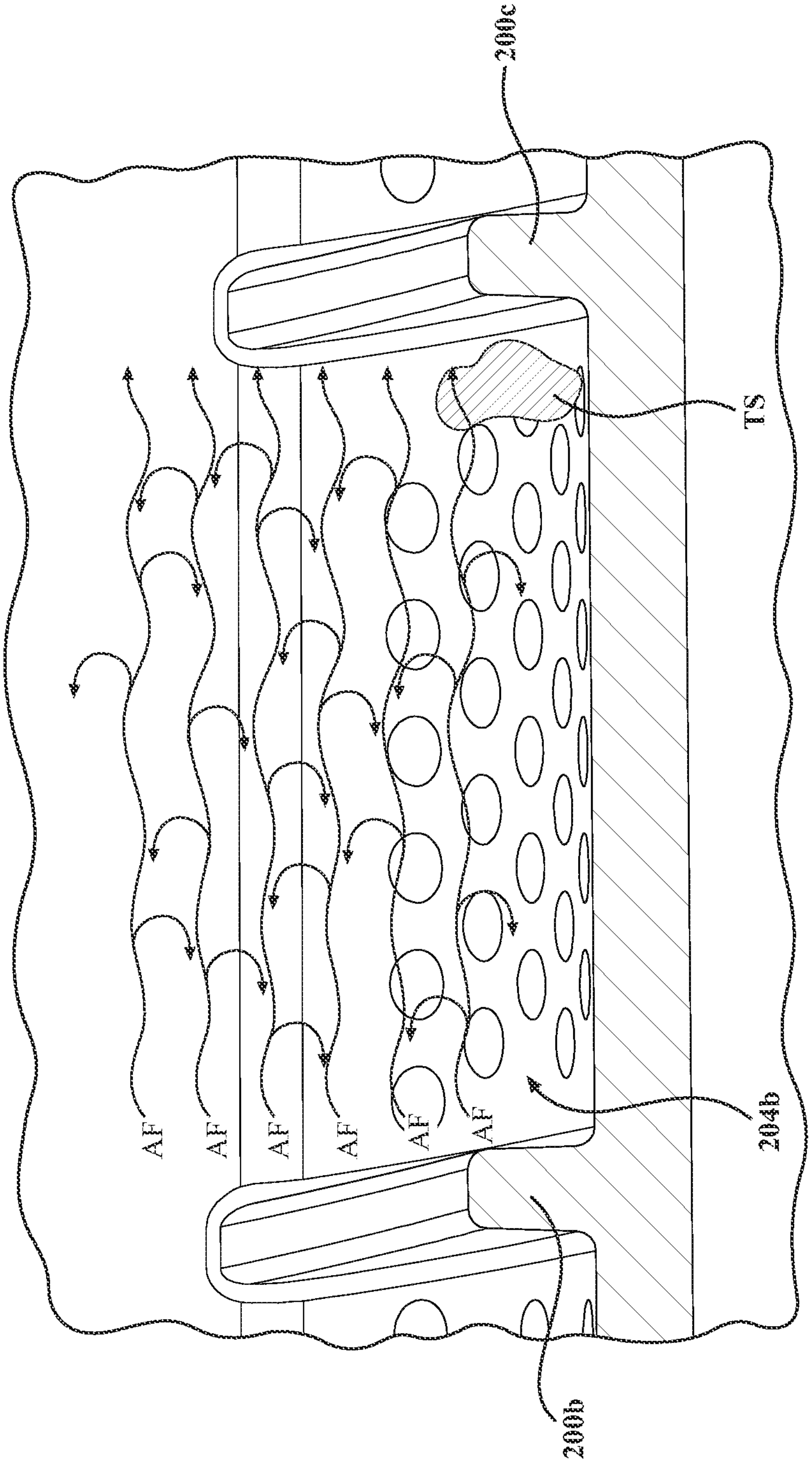
FIG. 15 is a detailed view of the portion of the manifold of FIG. 14 within detail 15-15.

As to be further described with relation to the sealing edge 212, the influence of the ribs 200*a*-200*c* on the airflow AF is introduced with reference to FIG. 15. In known systems, after the tray is partially removed, airflow rushes the tray in the distal direction and becomes turbulent within the tray 176. The turbulent airflow often causes a pinball-like effect of the collected tissue sample such as a tissue sample TS, for example, a polyp. The pinball-like effect of the tissue sample TS may cause it to eject from the tray through the exposed portion of the tray. As schematically represented in FIG. 15, as the airflow AF rushes distally within the tissue collecting cavity 182, negligible airflow encounters the low pressure region in the pocket 204*b* defined between the ribs 200*a*-200*c*. Further, in the illustrated example with only a portion of the tissue sample TS extending above the adjacent rib 200*c*, the airflow AF is more likely to contact an upper aspect of the tissue sample TS and thereby unlikely to have the necessary lift forces to cause the aforementioned pinball-like effect. Still further, the illustrated example shows the tissue sample TS abutting the rib 200*c* oriented transverse to the direction of the airflow AF, and the rib 200 may mechanically prevent movement of the collected tissue sample along the base portion 184 prior to, during, and after removal of the tray 176 from the accessory sleeve 113.

As previously mentioned, the porous features 186 are defined within the base portion 184, and the porous features 186 are in the suction path to collect the tissue sample. The porous features 186 may be arranged to further limit or prevent movement of the collected tissue sample along the base portion 184 prior to, during, and after removal of the tray 176 from the accessory sleeve 113. Referring again to FIGS. 9-11, the porous features 186 may be disposed between the ribs 200*a*-200*c*. The porous features 186 may be disposed within the first pocket 204*a*, the second pocket 204*b*, the third pocket 204*c*, and/or the fourth pocket 204*d*. In the illustrated implementation, the porous features 186 are disposed in each of the four pockets 204*a*-204*d*.

The porous features 186 may be arranged in groupings 214. As used herein, a grouping is defined to include more than two porous features equally spaced apart from one another by a first distance. The groupings 214 themselves are apart from one another by a second distance greater than the first distance. For illustration purposes, FIG. 11 shows a dashed line bounding a first grouping 214*a*, and another dashed line bounding a second grouping 214*b*. The first and second groupings 214*a*, 214*b* are separated from one another by a center aspect 216 of the base portion 184. A width of the center aspect 216 is greater than a spacing between the porous features 186 of the first and second groupings 214*a*, 214*b*. The first and second groupings 214*a*, 214*b* of the illustrated implementation each include five rows of the porous features 186 arranged longitudinally along the base portion 184. It should be appreciated that the groupings 214 may include two, three, four, or six or more rows of the porous features 186. Moreover, in the illustrated implementation, there are two groupings 214 in each of the pockets 204*a*-204*d*. Likewise, it should be appreciated that there may be three, four, or five or more groupings in the pockets 204. It is not necessary that the pockets 204 include the same number of groupings, and/or the groupings from pocket to pocket may vary based on, among other things, imparting the desired flow characteristics through the tissue collecting cavity 182.

Owing to the base portion 184 being arcuate and concave between the opposing side portions 185, the tissue sample TS is likely to descend to the center aspect 216 under the influence of gravity, as shown in FIG. 11. The lack of porous features 186 within the center aspect 216 reduces the likelihood of airflow moving upwardly through the porous features 186 lifts the tissue sample TS off of the base portion 184, and perhaps into the airflow AF moving distally within the tissue collecting cavity 182 (see FIG. 15). In at least this respect, the ribs 200*a*-200*c* and the groupings 214 cooperate to limit movement of the tissue sample TS within the basket 180 prior to, during, and after removal of the tray 176 from the accessory sleeve 113.

As previously described in detail, the flexible portion 160 of the sealing member 154, the necked region 172, and the gap G induce the second suction path SSP to be beneath the tray 176 when the manifold 100 is in the bleed configuration. The bleed configuration limits or eliminates the first suction path FSP when the upper region 170 of the sealing member 154 remains engaged with the accessory opening 111. Once the tray 176 is partially removed, however, such that the tissue collecting cavity 182 is exposed to the ambient (e.g., positioned proximal to the accessory opening 111), airflow AF may enter the tissue collecting cavity 182. The tray 176 of the present disclosure advantageous includes the sealing edge 212 configured to delay the onset of any airflow AF entering the tissue collecting cavity 182. The delayed onset of the airflow AF within the tissue collecting cavity 182, particularly in combination with the ribs 200*a*-200*c* and the second suction path SSP below the basket 180, prevents dislodging or ejecting of the collected tissue sample from the tray 176.

Figure 10:
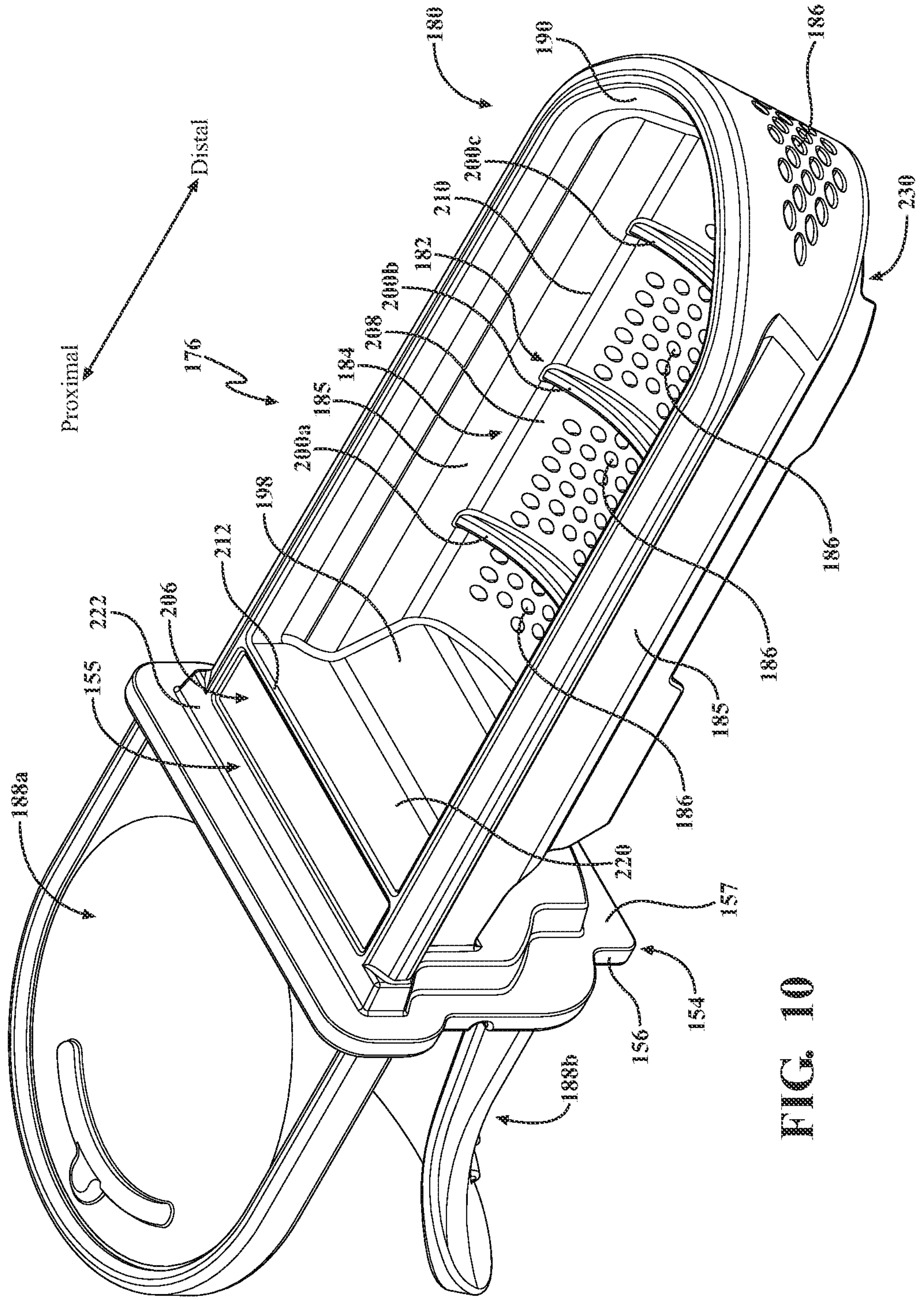
FIG. 10 is a top front perspective view of the tray of FIG. 9.

The sealing member 154 may include the shelf portion 155 extending distally from the flange portion 156, and the flange portion 156 includes the sealing surface 157. The shelf portion 155 includes the outer periphery sized slightly smaller than the accessory opening 111 so as to be positioned in sealing engagement with inner surfaces defining the accessory sleeve 113, one of which is a lower surface 218 of the upper barrier 103 (see FIGS. 12-14). In certain implementations, the proximal portion 206 previously introduced extends from the shelf portion 155. The proximal portion 206 may at least partially define the tissue collecting cavity 182. For example, FIG. 10 shows the proximal portion 206 including an upright surface 220 extending between the opposing side portions 185 and defining a proximal side of the tissue collecting cavity 182. The wall 198 may slope downwardly in the distal direction away from the upright surface 220.

Figure 12:
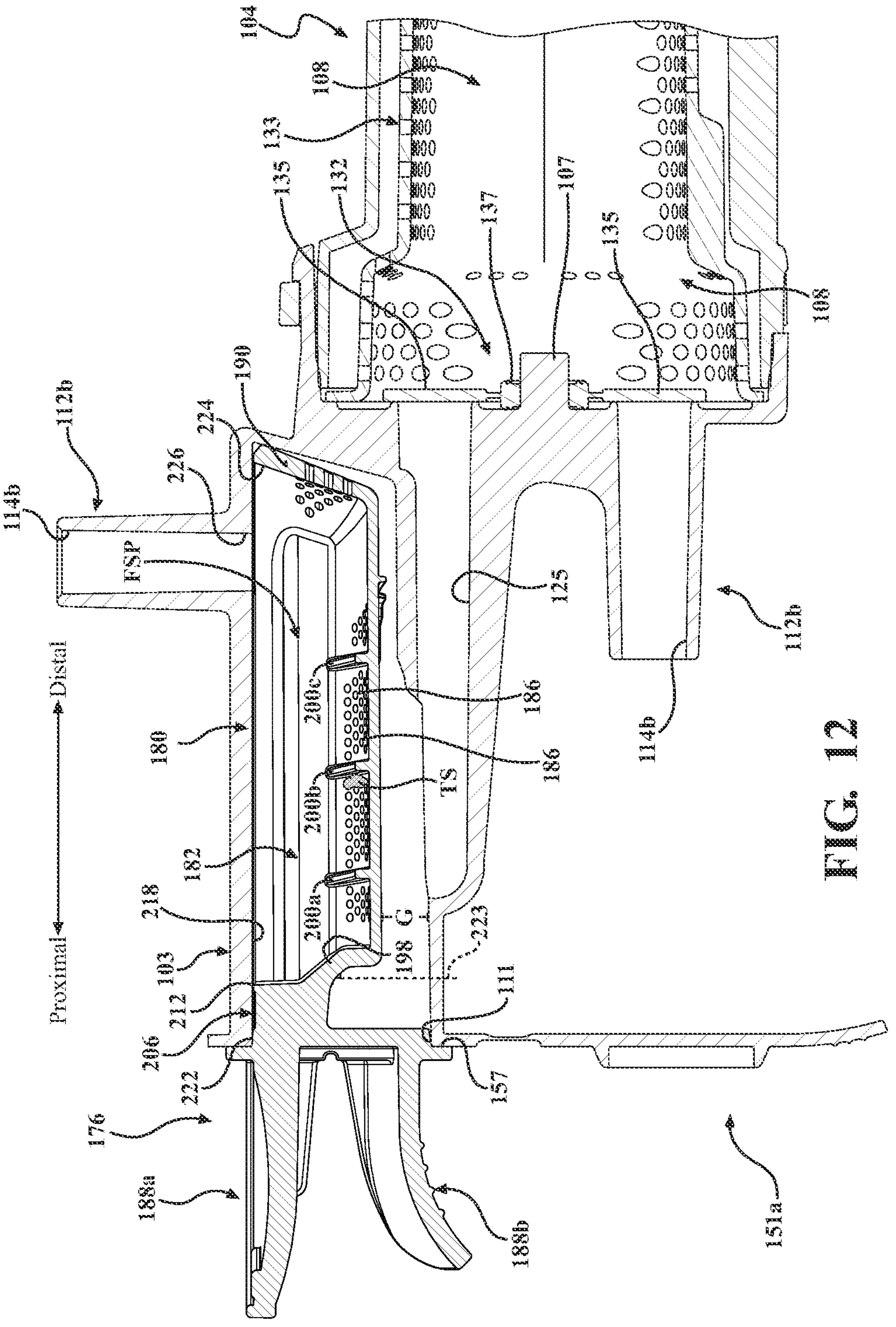
FIG. 12 is a sectional view of a portion of the manifold with the tray disposed within the sleeve in a first position and in the sealing configuration.

The proximal portion 206 includes the sealing edge 212. The sealing edge 212 may be considered the uppermost edge of the upright surface 220. Additionally or alternatively, the sealing edge 212 may be coplanar with an upper surface 222 of the shelf portion 155. In other words, the shelf portion 155 and the proximal portion 206 may be generally unitary in appearance, whereas otherwise the shelf portion 155 and the basket 180 may be discrete in appearance (but formed unitarily). The sealing edge 212 is spaced apart from the flange portion 156 so as to extend by a greater distance within the accessory sleeve 113 relative to the shelf portion when the tray 176 is removably positioned within the accessory sleeve 113. Referring to FIG. 12, the sealing edge 212 is in sealing engagement with the upper barrier 103 at a boundary line, identified as 223, that is appreciably more distal than the sealing engagement of the shelf portion 155 and the accessory opening 111. For example, a distance between the flange portion 156 and the sealing edge 212 may be at least three, five, seven, or nine or more millimeters.

Figure 13:
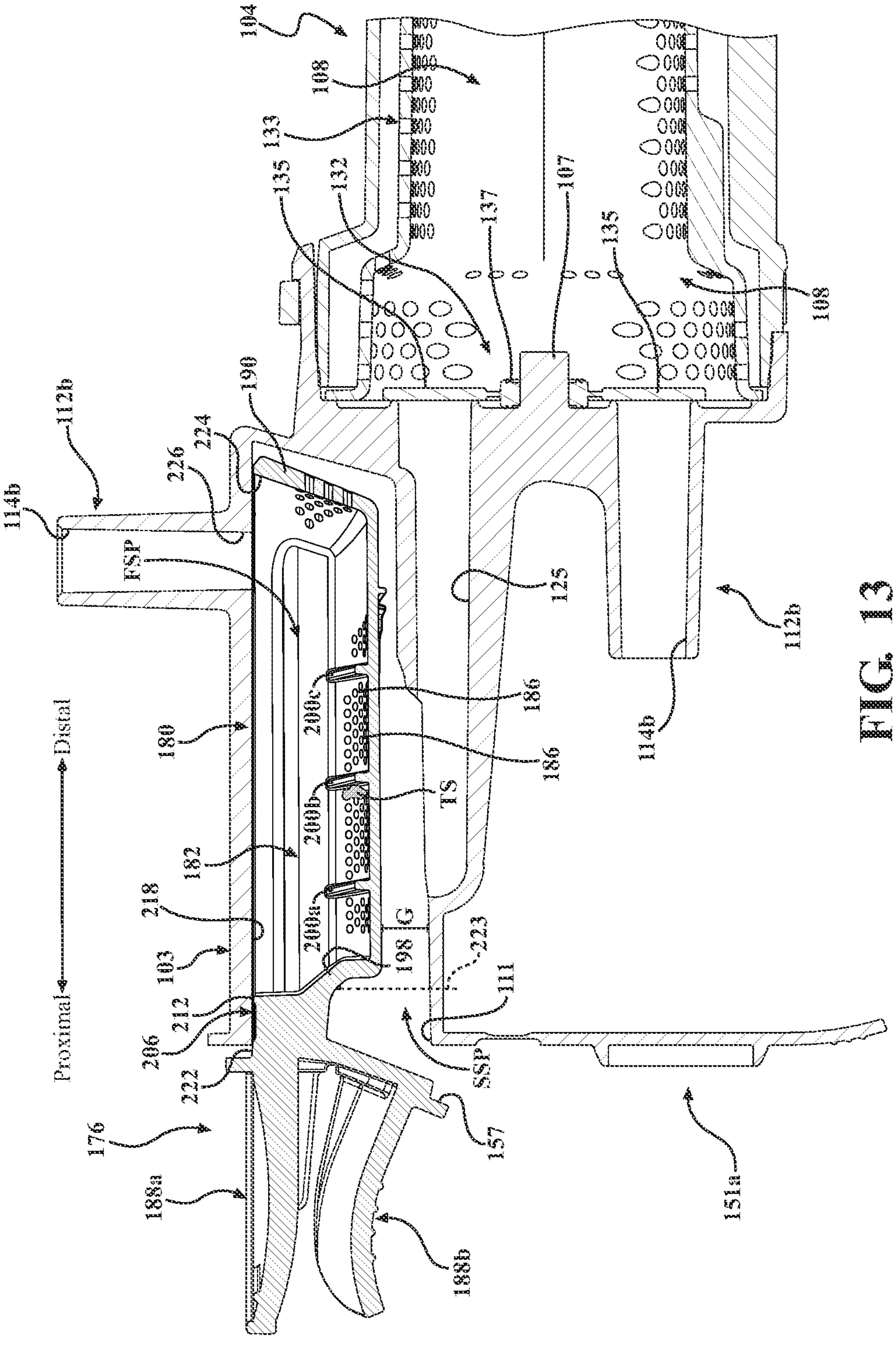
FIG. 13 is a sectional view of the portion of the manifold with the tray disposed within the 14 in a second position.
Figure 14:
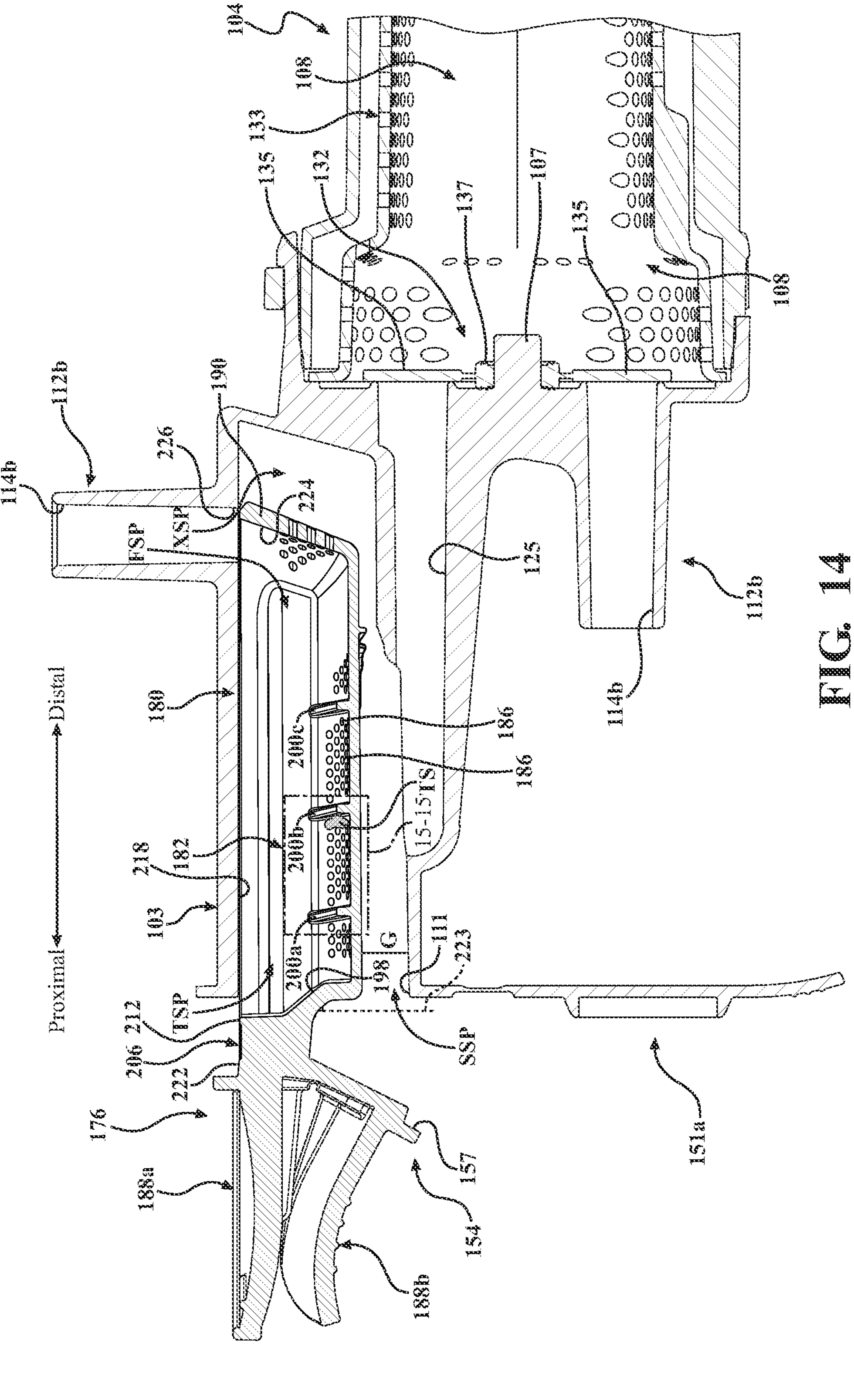
FIG. 14 is a sectional view of the portion of the manifold with the tray disposed within the sleeve in a second position.

The sealing edge 212 delays the onset of any airflow AF entering the tissue collecting cavity 182 as the tray 176 is removed from the accessory sleeve 113. FIG. 12 shows the tray 176 in a first or fully inserted position, and further shows the manifold 100 in the sealing configuration. An inner surface 224 of the distal portion 190 of the tray 176 is positioned distal to a distalmost aspect 226 of the inlet bore 114*a*. Thus, the first suction path FSP extends through the suction tube, the inlet bore 114*a*, the tissue collecting cavity 182, the transfer bore 125, and to the manifold volume 108 to the outlet opening 109. The collected tissue sample, namely the tissue sample TS, has been collected within the second pocket 204*b* adjacent the second rib 200*b*. FIG. 13 shows the tray 176 in a second position, and FIG. 14 shows the tray 176 in a third position. To move the tray 176 from the first position to the second position, the user applies an input to the first and second control members 118*a*, 118*b*, for example, pinching the grip to pull the tray 176 proximally. Owing to the flexible region 160 of the sealing member 154, the pinching input may momentarily move the manifold 100 from the sealing configuration to the bleed configuration (see, e.g., FIG. 8) prior to or simultaneously with the tray 176 beginning to move proximally within the accessory sleeve 113.

FIG. 13 shows the tray 176 positioned more proximal in the second position than the first position. In addition to the space between the sealing surface 157 and the accessory opening 111 created by moving the manifold 100 to the bleed configuration, further clearance is provided by the proximal movement of the tray 176 within the accessory sleeve 113. Nearly an entire of the airflow may be through the second suction path SSP with only minimal or negligible airflow through the first suction path FSP. The sealing edge 212 remains in sealing engagement with the lower surface 218 of the upper barrier 103. Therefore, in the second position, airflow is prevented from entering the tissue collecting cavity 182. In the illustration, the tissue sample TS remains within the second pocket 204*b* adjacent the second rib 200*b*, and the inner surface 224 of the distal portion 190 of the tray 176 remains positioned distal to the distalmost aspect 226 of the inlet bore 114*a*.

FIG. 14 shows the tray 176 in the third position—more proximal to the first and second positions—in which even greater clearance is provided between the sealing surface 157 and the accessory opening 111. The sealing edge 212 is no longer in sealing engagement with the lower surface 218 of the upper barrier 103. In other words, the sealing edge 212 has been moved proximal to the accessory opening 111, and now at least a portion of the tissue collecting cavity 182 is exposed to the ambient. A third suction path TSP may be provided, in particular the airflow entering the tissue collecting cavity 182 between the sealing edge 212 and the upper barrier 103. Despite the presence of the third suction path TSP, movement of the tissue sample TS may be minimized or eliminated based on any one or more of the following advantageous features: (i) the ribs 200*a*-200*c* defining the pockets 204*a*-204*d* providing the low pressure regions (see FIG. 15), (ii) the ribs 200*a*-200*c* providing a barrier, and (iii) the base portion 184 that is arcuate with the center aspect 216 between the groupings 214 of the porous features 186.

Once the sealing edge 212 is no longer in sealing engagement with the upper barrier 103, the inner surface 224 of the distal portion 190 of the tray 176 is no longer positioned distal to the distalmost aspect 226 of the inlet bore 114*a*. In other words, the distal portion 190 begins to cross the inlet bore 114*a* as the tissue collecting cavity 182 becomes exposed to the ambient. Among other advantages, the arrangement prevents the tissue sample TS from ejecting over the distal portion 190 should the tissue sample TS be moving within the tray 176. Furthermore, the distal portion 190 crossing the inlet bore 114*a* effectively eliminates the first suction path FSP and generates a fourth suction path XSP. The fourth section path XSP extends through the suction tube, the inlet bore 114*a*, the accessory sleeve 113 distal to the tray 176, the transfer bore 125, and to the manifold volume 108 to the outlet opening 109. The tray 176 may include a distal slot 230 within the foot 131 (see FIG. 10) to accommodate the fourth suction path XSP to move from the accessory sleeve 113 to the transfer bore 125. Therefore, despite the presence of the third suction path TSP within the tissue collecting cavity 182, the volumetric flow rates of air permitted by the second suction path SSP and the fourth suction path XSP are appreciably greater relative to the third suction path TSP, and fluid dynamics dictate (i.e., path of least resistance) that the third suction path TSP may have relatively minor volumetric flow rates and forces to disrupt the collected tissue sample. Particularly in combination with the ribs 200*a*-200*c* and the groupings 214 of the porous features 186, the user may confidently remove the tray 176 with minimal risk of inadvertently losing the collected tissue sample.

In certain implementations, the cap portion 106 and the trunk 104 are removably coupled to one another. Referring to FIGS. 1 and 2, the cap portion 106 includes at least one key 146 or head coupler configured to be removably coupled with at least one keyway 148 or trunk coupler of the trunk 104. The key 146 may be plural keys 146 diametrically opposed to one another and extending proximally from the cap portion 106. The keyway 148 may be plural keyways 148 diametrically opposed to one another. The key may include a shank, and a barb extending from the shank. The barb may be thicker than the shank. As a result, during assembly of the manifold 100 or when it is desired to couple the cap portion 106 with the trunk 104, the cap portion 106 is oriented relative to the trunk 104 such that the barb(s) 164 are rotationally aligned with insertion portion(s) of the keyways 148. After the barb(s) extend through the insertion portion(s), the cap portion 106 is rotated relative to the trunk 104, to move the key(s) 146 within the keyway(s) 148 into in an interference arrangement. The interference prevents axial movement of the cap portion 106 relative to the trunk 104, and the cap portion 106 may be considered secured to the trunk 104 to form the housing 102 of the manifold 100.

The cap portion 106 and/or the trunk 104 may include indicia 150, 152 arranged to indicate whether the cap portion 106 and the trunk 104 are in a locked configuration in which the cap portion 106 is secured to the trunk 104, or an unlocked configuration in which the cap portion 106 may be decoupled from the trunk 104. More particularly, in the locked configuration, the keys 146 may be engaging the keyways 148 to prevent axial movement of the cap portion 106 relative to the trunk 104 as described above. The indicia 150 on the cap portion 106 may include a lock icon and an unlocked icon, as shown in FIGS. 1 and 2, and the indicia 150 on the trunk 104 may include an arrow configured to be adjacent and pointing towards one of the locked and unlocked icons depending on whether the manifold 100 is in the locked or unlocked configuration. Of course, the reverse arrangement is contemplated. FIGS. 1 and 2 show the manifold 100 in the locked configuration with the arrow adjacent to and pointing towards the locked icon. With relative rotation of the cap portion 106 and the trunk 106 as previously described, the arrow is moved relative to the cap portion 106 to be positioned adjacent to and pointing towards the unlocked icon.

The removable coupling between the cap portion 106 and the trunk 104 may provide access to the manifold volume 108 within which the filter element 133 is disposed. Among other advantages, accessing the filter element 133 may allow the user to retrieve waste material collected within the filter element 133, most notably a polyp or tissue sample, for further examination and processing during certain surgical procedures. Commonly-owned International Publication No. WO 2013/090579, published Jun. 20, 2013, the entire contents of which is hereby incorporated by reference, discloses a manifold including a tissue trap for collecting the polyp or the tissue sample. In certain implementations, the manifold 100, including the cap portion 106, may include further features to facilitate collection of tissue sample(s). When it is desired to decouple the cap portion 106 from the trunk 104, the aforementioned method steps are reversed, and the manifold volume 108 of the trunk 104 may be accessed.

In certain implementations, the cap portion 106 and the trunk 104 are rigidly connected through a suitable joining process, for example, spin welding, solvent bonding, adhesives, mechanical fastening, and the like. As previously mentioned, the housing 102 may be of unitary or monolithic construction such that there is no discrete head and trunk. Suitable manufacturing processes for forming the housing 102 may include injection molding, three-dimensional printing, computer numerical control (CNC) machining, polymer casting, vacuum forming, blow molding, among others. Suitable materials for forming the housing 102 may include polymers, composites, metals, ceramics, and combinations thereof. The materials include sufficient anticorrosive properties to avoid degradation when exposed to the waste material and sufficient mechanical properties to maintain integrity under the vacuum levels to be provided by the medical waste collection system. The polymers of polyethylene, polypropylene, polyvinyl chloride, polyethylene terephthalate (PET, PETE), polystyrene, polycarbonate, and poly(methyl methacrylate) may be particularly well suited for the manifold 100 in low-cost and disposable implementations.

Certain implementations may be described with reference to the following exemplary clauses:

Clause 1—A tray configured to be removably positioned within a sleeve having an opening and to collect a tissue sample drawn through a first suction path, the tray including: a sealing member configured to be positioned in sealing engagement with the opening when the tray is removably positioned within the sleeve, wherein the sealing member includes a resiliently flexible portion; a first control member extending from the sealing member; a second control member extending from the sealing member and spaced apart from the first control member; a basket extending from the sealing member in a direction opposite the first and second control members, the basket defining porous features for collecting the tissue sample from a liquid drawn through the first suction path; and wherein the first and second control members are positioned opposite the resiliently flexible portion and configured to receive an input to resiliently and pivotably move at least a portion of the sealing member away from the opening to provide a second suction path through the opening and the sleeve.

Clause 2—The tray of clause 1, wherein the basket includes a necked region having a reduced sectional profile of the basket such that a void space is defined between the basket and the sealing member.

Clause 3—The tray of clauses 1 or 2, wherein the basket includes a base and opposing side portions coupled to the base to collectively define a tissue collecting cavity with the porous features defined within the base, wherein the base is arcuate in shape and concave between the opposing side portions.

Clause 4—The tray of any one of clauses 1-3, further including opposing rails extending along the base and configured to channel the second suction path.

Clause 5—The tray of clause 4, wherein each of the opposing rails defines a slot.

Clause 6—The tray of any one of clauses 1-5, wherein the resiliently flexible portion includes a living hinge including a reduced thickness portion of the sealing member.

Clause 7—A tray configured to be removably positioned within a sleeve having an opening and to collect a tissue sample drawn through a first suction path, the tray including: a sealing member configured to be positioned in sealing engagement with the opening when the tray is removably positioned within the sleeve, wherein the sealing member includes an upper region and a lower region; a first control member extending from the upper region; a second control member extending from the lower region and spaced apart from the first control member; and a basket extending from the upper region in a direction opposite the first control member, the basket defining porous features for collecting the tissue sample, wherein no portion of the basket extends from the lower region of the sealing member, wherein the first and second control members are configured to receive an input to pivot the lower region relative to the upper region to move the lower region of the sealing member away from the opening to provide a second suction path through the opening and the sleeve without disturbing the collected tissue sample.

Clause 8—The tray of clause 7, wherein the basket includes a necked region having a reduced sectional profile of the basket such that a void space is defined between the basket and the lower region of the sealing member.

Clause 9—The tray of clauses 7 or 8, wherein the basket includes a base and opposing side portions coupled to the base to collectively define a tissue collecting cavity with the porous features defined within the base, the tray further including opposing rails extending along the base and configured to channel the second suction path.

Clause 10—The tray of clause 9, wherein each of the opposing rails defines a slot.

Clause 11—A tray configured to be removably positioned within a sleeve having an opening and to collect a tissue sample drawn through a first suction path, the tray including: a sealing member configured to be positioned in sealing engagement with the opening when the tray is removably positioned within the sleeve, wherein the sealing member includes an upper region and a lower region separated by a living hinge including a reduced thickness portion of the sealing member; a control member extending from the upper region; and a basket extending from the sealing member in a direction opposite the control member, the basket including porous features for collecting the tissue sample, wherein the control member is configured to receive an input to pivot the lower region relative to the upper region about the living hinge to move the lower region of the sealing member away from the opening to provide a second suction path through the opening and the sleeve.

Clause 12—The tray of clause 11, wherein the basket includes a necked region having a reduced sectional profile of the basket such that a void space is defined between the basket and the sealing member.

Clause 13—The tray of clauses 11 or 12, wherein the basket includes a base and opposing side portions coupled to the base to collectively define a tissue collecting cavity with the porous features defined within the base, wherein the base is arcuate in shape and concave between the opposing side portions.

Clause 14—The tray of any one of clauses 11-13, further including opposing rails extending along the base and configured to channel the second suction path.

Clause 15—The tray of clause 14, wherein each of the opposing rails defines a slot.

Clause 16—A tray for collecting a tissue sample drawn under influence of suction, the tray configured to be removably positioned within a sleeve having an opening, the tray including: a sealing member configured to be positioned in sealing engagement with the opening when the tray is removably positioned within the sleeve; a control member extending from the sealing member; a basket coupled to the sealing member and including a base, opposing side portions coupled to the base to collectively define a tissue collecting cavity, and porous features defined within the base for collecting the tissue sample, wherein the basket has a first sectional profile defined by the base portion, the opposing side portions, and a boundary between an upper aspect of the opposing side portions; the basket further including a necked region extending from the sealing member in a direction opposite the control member, the necked region having a second sectional profile defined between a lower transition surface of the necked region and the upper aspect of the opposing side portions, wherein the second sectional profile is smaller than the first sectional profile such that a void space is defined between the tissue collecting cavity and the sealing member.

Clause 17—The tray of clause 16, wherein the base is arcuate in shape and concave between the opposing side portions.

Clause 18—The tray of clauses 16 or 17, further including opposing rails extending along the base.

Clause 19—The tray of clause 18, wherein each of the opposing rails defines a slot.

Clause 20—A tray configured to be removably positioned within a sleeve having an opening and to collect a tissue sample drawn through a first suction path, the tray including: a sealing member configured to be positioned in sealing engagement with the opening when the tray is removably positioned within the sleeve, wherein the sealing member includes a resiliently flexible portion; a control member extending from the sealing member and configured to receive an input to resiliently and pivotably move at least a portion of the sealing member away from the opening to provide a second suction path through the opening and the sleeve; and a basket coupled to the sealing member and including a base, opposing side portions coupled to the base to collectively define a tissue collecting cavity, porous features within the base portion for collecting the tissue sample, and a foot including opposing rails extending along the base in a direction away from the tissue collecting cavity, wherein the foot is configured to channel the second suction path.

Clause 21—The tray of clause 20, wherein each of the opposing rails defines a slot.

Clause 22—The tray of any one of clauses 1-21, wherein the basket further includes a wall collectively define a tissue collecting cavity with the wall configured to position the tissue sample away from the sealing member so as to be visible through the sleeve when viewed from above.

Clause 23—The tray of any one of clauses 1-22, further including a distal end portion extending from the base and between the opposing side portions, wherein the distal end portion includes additional porous features.

Clause 24—A manifold for collecting a tissue sample through a suction tube, the manifold including: a sleeve including an upper barrier that is at least partially transparent; a tray including: a sealing member configured to be positioned in sealing engagement with the opening when the tray is removably positioned within the sleeve; a control member extending from the sealing member; and a basket extending from the sealing member in a direction opposite the control member, the basket including a base that is opaque and defining porous features for collecting the tissue sample, opposing side portions extending from the base, and a wall extending downwardly away from the sealing member, wherein the base, the opposing sides, and the wall collectively define a tissue collecting cavity with the wall configured to position the tissue sample away from the sealing member so as to be visible through the upper barrier when viewed from above.

Clause 25—The manifold of clause 24, wherein the wall is a ramp that slopes downwardly away from the sealing member so as to cause the tissue sample to descend towards the base.

Clause 26—The manifold of clause 24 or 25, wherein the sleeve includes shelf portions defining a trough therebetween, wherein the second suction path extends through the trough.

Clause 27—A manifold for collecting the tissue sample through a suction tube, the manifold including: the tray of any one of clauses 1-22; and the sleeve.

Clause 28—A method of collecting a sample under influence of a vacuum from a medical waste collection assembly including a receiver, said method comprising: coupling a suction tube to an inlet fitting of a manifold that defines an inlet bore; positioning the manifold within an opening of the receiver, wherein a tray is removably disposed within a sleeve in a first position such that (i) a sealing member of the tray is positioned in sealing engagement with an opening, (ii) a distal portion of the tray is positioned distal to the inlet bore, and (iii) a tissue collecting cavity of the tray opens towards the inlet bore; operating the medical waste collection assembly with the tray in the first position, wherein the sample is drawn through a first suction path into the tissue collecting cavity; providing an input to first and second control members to resiliently move the first and second control members towards one another, wherein a lower portion of the sealing member moves away from the opening to provide a second suction path; maintaining the input to the first and second control members while moving the tray from the first position to a second position in which the sealing member moves away from the opening and a sealing edge of the tray remains in sealing engagement with an upper barrier defining the sleeve, wherein the distal portion of the tray remains positioned distal to the inlet bore in the second position; and maintaining the input to the first and second control members while moving the tray from the second position to a third position in which the sealing member moves further away from the opening and the sealing edge of the tray disengages the upper barrier defining the sleeve to provide a third suction path, wherein the distal portion of the tray moves proximal to the inlet bore in the third position to eliminate the first suction path and provide a fourth suction path.

Clause 29—The method of clause 28, wherein the steps of providing the input to first and second control members and the moving of the tray from the first position to the second position are performed simultaneously.

The foregoing description is not intended to be exhaustive or limit the invention to any particular form. The terminology which has been used is intended to be in the nature of words of description rather than of limitation. Many modifications and variations are possible in light of the above teachings and the invention may be practiced otherwise than as specifically described.

What is claimed is:

1. A tray configured to collect a tissue sample under influence of a vacuum by being removably positioned within a sleeve having an opening, said tray comprising:

a sealing member configured to be positioned in sealing engagement with the opening when said tray is removably positioned within the sleeve; and a basket extending from said sealing member and comprising a base portion, a distal portion opposite said sealing member, and opposing side portions coupled to said base portion to collectively define a tissue collecting cavity, said base portion defining porous features for collecting the tissue sample with said tissue collecting cavity, wherein a longitudinal axis of said tray is defined between said sealing member and said distal portion, wherein said base portion comprises ribs disposed within said tissue collecting cavity, and wherein said ribs are elongate and oriented on an axis transverse to said longitudinal axis, wherein said base portion is arcuate in shape and concave between said opposing side portions, and wherein said ribs are arcuate and contoured complementary to said arcuate shape of said base portion.

2. The tray of claim 1, wherein said porous features are positioned between said ribs.

3. The tray of claim 1, wherein said ribs further comprises three ribs.

4. The tray of claim 1, wherein the ribs are crescent-shaped.

5. A tray configured to collect a tissue sample under influence of a vacuum by being removably positioned within a sleeve having an opening, said tray comprising:

a sealing member configured to be positioned in sealing engagement with the opening when said tray is removably positioned within the sleeve; and a basket extending from said sealing member and comprising a base portion, a distal portion opposite said sealing member, and opposing side portions coupled to said base portion to collectively define a tissue collecting cavity, said base portion defining porous features for collecting the tissue sample with said tissue collecting cavity, wherein a longitudinal axis of said tray is defined between said sealing member and said distal portion, wherein said base portion is defined between an upper surface opposite a lower surface, and comprises a rib that is crescent-shaped and oriented on an axis transverse to said longitudinal axis, and wherein said crescent-shaped rib extends upwardly from said upper surface by a distance sufficient to create a pocket that is a low pressure region as said tray is removed from within the sleeve.

6. The tray of claim 5, wherein said basket has a length greater than a width such that said basket is elongate.

7. The tray of claim 5, wherein the rib further comprises three ribs.

8. The tray of claim 7, wherein said three ribs are equally spaced apart from one another.

9. The tray of claim 7, wherein said three ribs define four pockets of said base portion, wherein porous features are within each of said four pockets.

10. The tray of claim 7, wherein said three ribs are parallel to one another.

11. The tray of claim 5, wherein said porous features are arranged in at least two groupings.

12. The tray of claim 11, wherein each of said at least two groupings comprises at least two rows of said pores oriented longitudinally along said base portion.

13. The tray of claim 11, wherein said ribs separate said at least two groupings.

14. The tray of claim 5, further comprising a first control member extending from an upper region of the sealing member and a second control member extending from a lower region of the sealing member spaced apart from the first control member, and wherein the first and second control members are configured to receive an input to pivot the lower region relative to the upper region to move the lower region of the sealing member away from the opening.

15. The tray of claim 14, wherein the basket extends from the upper region in a direction opposite the first control member, and wherein no portion of the basket extends from the lower region of the sealing member.

16. A tray configured to collect a tissue sample under influence of a vacuum by being removably positioned within a sleeve having an opening, said tray comprising:

a sealing member configured to be positioned in sealing engagement with the opening when said tray is removably positioned within the sleeve; and a basket comprising a proximal portion extending from said sealing member, opposing side portions coupled to said proximal portion, a base portion coupled to said opposing side portions, and a distal portion coupled to said base portion and said opposing side portions, wherein said proximal portion, opposing side portions, said base portion, and said distal portion collectively define a tissue collecting cavity with said base portion defining porous features for collecting the tissue sample with said tissue collecting cavity, and wherein a longitudinal axis of said tray is defined between said sealing member and said distal portion, a rib defining at least two pockets within said tissue collecting cavity, wherein said at least two pockets are arranged in series between said proximal portion and said distal portion and associated with low pressure regions as said tray is removed from within the sleeve, wherein said base portion is arcuate in shape and concave between said opposing side portions, and wherein said rib is arcuate and contoured complementary to said arcuate shape of said base portion.

17. The tray of claim 16, wherein said at least two pockets comprises four pockets.

18. The tray of claim 16, wherein one of said pockets is defined between the rib and said proximal portion.

19. The tray of claim 16, wherein one of said pockets is defined between the rib and said distal portion.

20. The tray of claim 16, wherein said rib is crescent-shaped.

* * * * *